(12) United States Patent
Hsiao et al.

(10) Patent No.: US 12,359,259 B2
(45) Date of Patent: Jul. 15, 2025

(54) BIOMARKERS FOR PREDICTING PROSTATE CANCER PROGRESSION

(71) Applicant: ACADEMIA SINICA, Taipei (TW)

(72) Inventors: Pei-Wen Hsiao, Taipei (TW); Chin-Hsien Tsai, Taipei (TW); Sheue-Fen Tzeng, Taipei (TW); Shih-Chuan Hsieh, Jiaoxi Township (TW); Ming-Shyue Lee, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 1232 days.

(21) Appl. No.: 16/972,984

(22) PCT Filed: Jun. 10, 2019

(86) PCT No.: PCT/US2019/036264
§ 371 (c)(1),
(2) Date: Dec. 7, 2020

(87) PCT Pub. No.: WO2019/237098
PCT Pub. Date: Dec. 12, 2019

(65) Prior Publication Data
US 2021/0254168 A1    Aug. 19, 2021

Related U.S. Application Data

(60) Provisional application No. 62/682,410, filed on Jun. 8, 2018.

(51) Int. Cl.
*C12Q 1/6886*    (2018.01)
*G01N 33/574*    (2006.01)

(52) U.S. Cl.
CPC ..... *C12Q 1/6886* (2013.01); *G01N 33/57434* (2013.01); *C12Q 2600/118* (2013.01); *C12Q 2600/158* (2013.01); *G01N 2333/91091* (2013.01); *G01N 2800/52* (2013.01)

(58) Field of Classification Search
None
See application file for complete search history.

(56) References Cited

U.S. PATENT DOCUMENTS

| 2014/0220580 A1 | 8/2014 | Brown et al. |
| 2014/0228233 A1 | 8/2014 | Pawlowski et al. |
| 2015/0301058 A1 | 10/2015 | Schettini et al. |

OTHER PUBLICATIONS

Ferreira et al., "Glycosylation as a Main Regulator of Growth and Death Factor Receptors Signaling", International Journal of Molecular Sciences, 2018, 19, 580, pp. 1-28.
International Search Report for PCT/US2019/036264 (PCT/ISA/210) mailed on Sep. 30, 2019.
Tsai et al., "Metastatic Progression of Prostate Cancer Is Mediated by Autonomous Binding of Galectin-4-O-Glycan to Cancer Cells", Molecular and Cellular Pathobiology, Cancer Research; 76(19), Oct. 1, 2016, pp. 5756-5767, total of 14 pages.
Tzeng et al., "O-Glycosylation-mediated signaling circuit drives metastatic castration-resistant prostate cancer", The FASEB Journal, Research, www.fasebj.org, vol. 32, Dec. 2018, pp. 6869-6879.
Written Opinion of the International Searching Authority for PCT/US2019/036264 (PCT/ISA/237) mailed on Sep. 30, 2019.

*Primary Examiner* — Nancy J Leith
(74) *Attorney, Agent, or Firm* — Birch, Stewart, Kolasch & Birch, LLP

(57) ABSTRACT

The present invention relates to biomarkers, methods and assay kits for predicting prognosis and/or monitoring progression of prostate cancer. The biomarkers include a glycosyltransferases [core 1 beta-3-galactosyltransferase (C1GALT1) and/or ST3 beta-galactoside alpha-2,3-sialyltransferase 1 (ST3GAL1)] gene product, its saccharide substrate/product, and/or a galectin-4 gene product.

14 Claims, 25 Drawing Sheets

Specification includes a Sequence Listing.

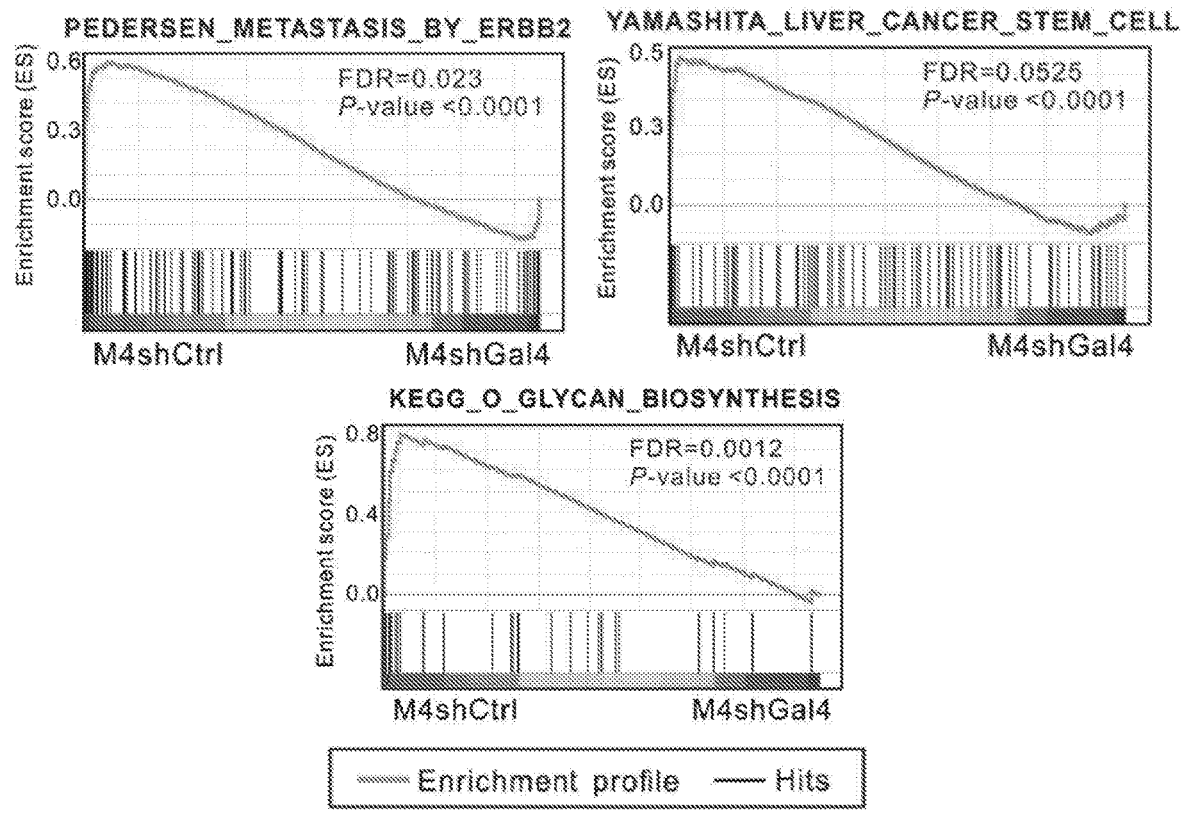
Fig. 5A
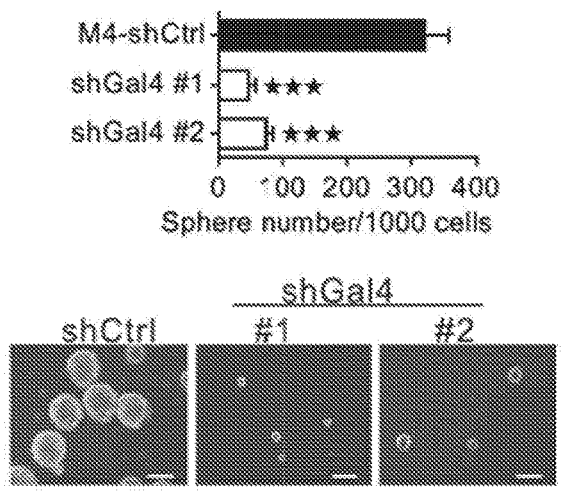 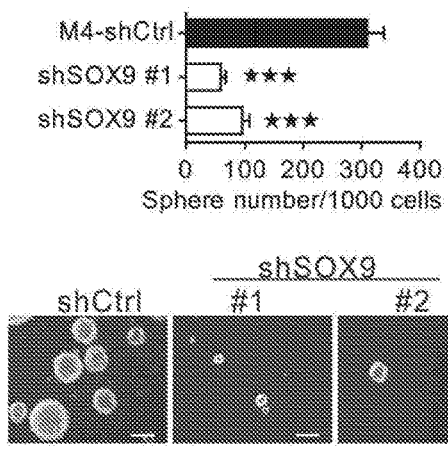
Fig. 5B	Fig. 5C

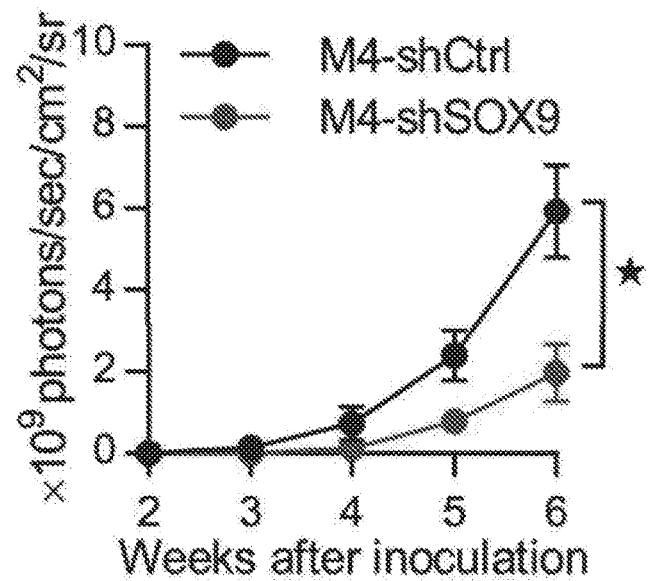
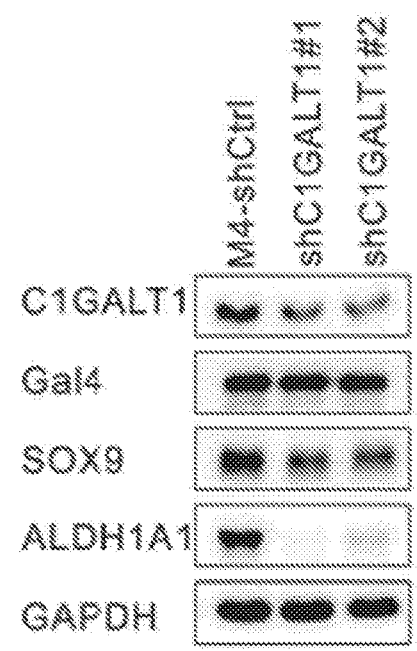
Fig. 5D    Fig. 5E
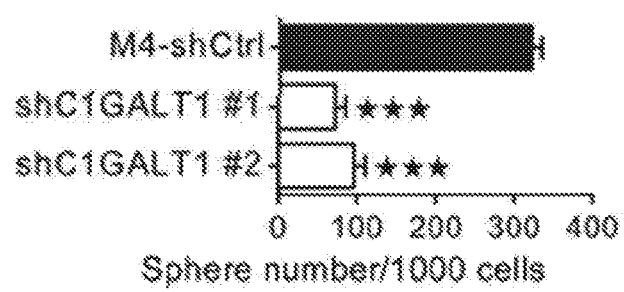
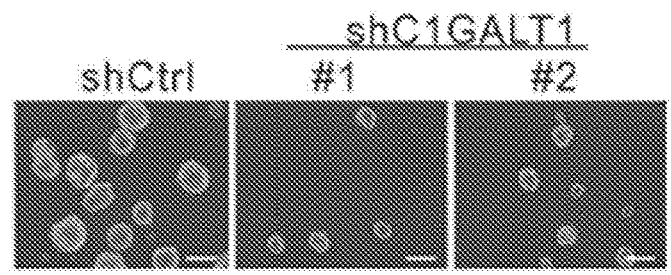
Fig. 5F

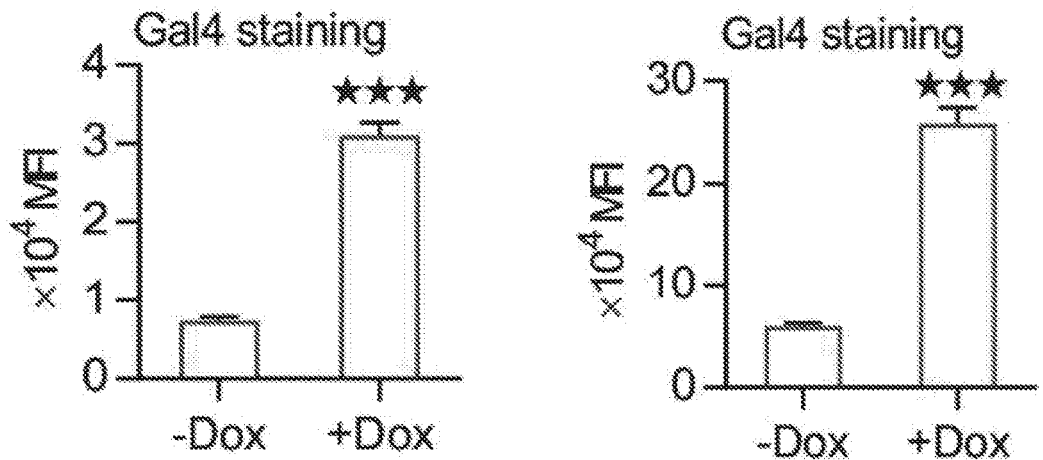
Fig. 6G
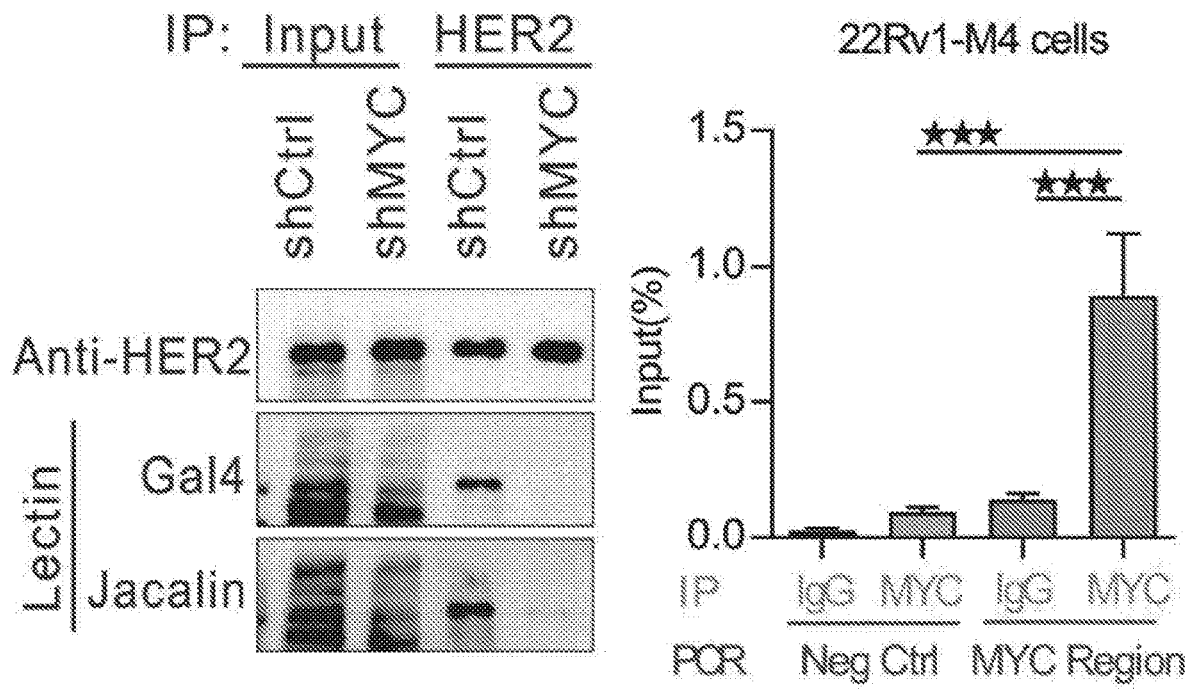
Fig. 6H
Fig. 6I

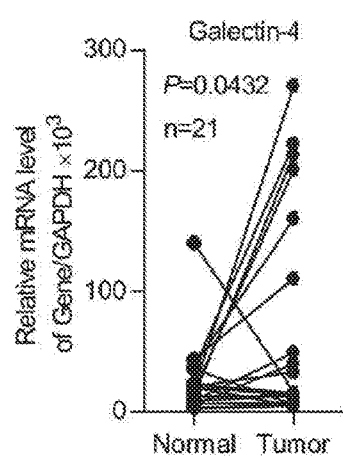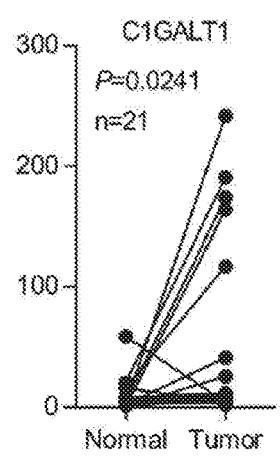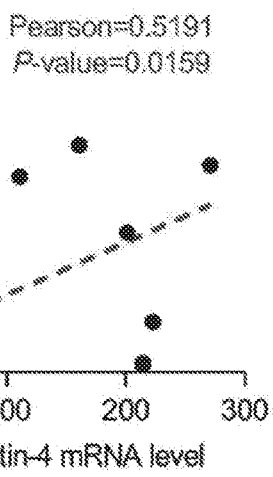
Fig. 7A
Fig. 7B
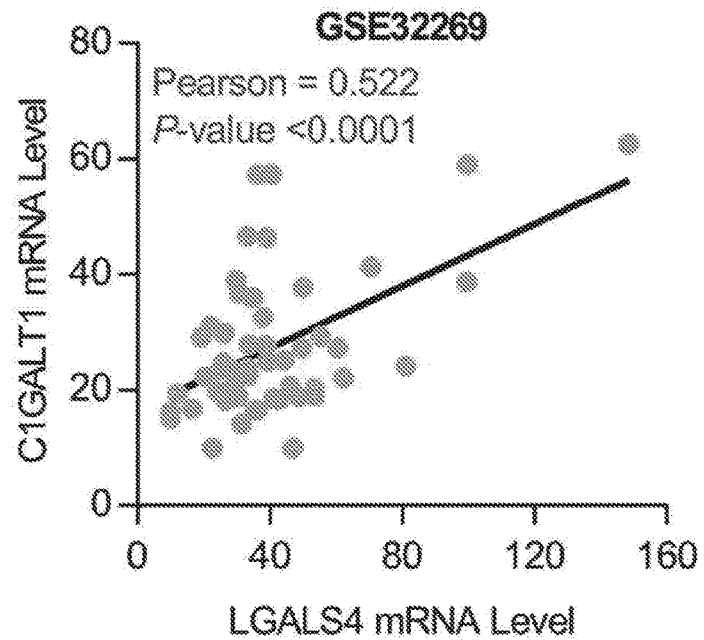
Fig. 7C

BIOMARKERS FOR PREDICTING PROSTATE CANCER PROGRESSION

RELATED APPLICATIONS

This application claims the benefit of U.S. provisional application No. 62/682,410, filed Jun. 8, 2018 under 35 U.S.C. § 119, the entire content of which is incorporated herein by reference.

TECHNOLOGY FIELD

The present invention relates to biomarkers, methods and assay kits for predicting prognosis and/or monitoring progression of prostate cancer.

BACKGROUND OF THE INVENTION

Androgen deprivation therapy (ADT) represents the backbone of advanced prostate cancer (PCa) treatment due to the critical role of androgen receptor (AR) signaling in the pathogenesis of PCa. However, in most patients, treatment with ADT, such as first-line with leuprolide, goserelin, or bicalutamide, and second-line with abiraterone or enzalutamide, eventually leads to castration-resistant PCa (CRPC) and the further development of lethal metastatic disease, mCRPC (1). Upregulation of HER2 expression was found during the disease progression to CRPC; and aberrant HER2 signaling activities by forced expression of HER2 in cell lines and xenograft models led to tumor growth of CRPC, in which HER2/HER3 was found to promote AR protein stability and transcriptional activity (2-4). HER2 activation was found elevated in a subset of patients with abiraterone-resistant PCa, possibly due to compensation for the loss of androgen signaling (5). However, clinical trials of HER2-targeted therapies have not been effective in CRPC patients (6-8).

Cumulative evidence showed altered glycosylation accompanied by the acquisition of cellular features required for tumor progression, indicating tumor-associated glycans are potentially valuable as diagnostic or therapeutic targets (9). Glycosylation is remarkably dynamic and commonly altered in cancer, leading to the expression of cancer-associated antigens, sometimes referred to as oncofetal antigens that recapitulate expression normally limited to embryonic tissues. Several glycans on the tumor surface, such as Tn, sialyl-Tn, and T antigen have been identified as mediating critical pathophysiological events during the various steps of tumor progression, such as cell cycle dysregulation, cell adhesion, invasion activity, and angiogenesis (9, 10). For example, upregulation of fucosylation by FUT8 in melanoma drives invasion and metastasis (11). Tumor-associated carbohydrates have been linked to drug resistance in multiple in vitro models (12) and also indicated as a prognostic marker to predict therapeutic efficacy in breast cancer patients who were treated with anthracycline-containing adjuvant chemotherapy (13). Among the oncofetal glycan antigens, Galß1-3GalNAcα disaccharide (T antigen or CD176) is highly expressed in about 60-90% carcinomas of prostate, breast, colon, and stomach (14). The T antigen of mucin-type core 1 O-glycans is synthesized by transferring a galactose (Gal) residue from UDP-Gal to N-acetylgalactosamine (GalNAc)-conjugated protein by C1GALT1 whose correct folding and localization depend on the chaperone activity of C1GALT1C1 (COSMC). T antigen expression on the surface of metastatic lung cancer cells promotes metastasis through interactions with galectin-3-carrying myeloid cells in the metastatic niche (15). Notably, co-expression of T antigen with CD44 or CD133, markers of cancer stem cells, has been identified in lung, breast, and liver cancers (16). Despite considerable evidence showing a positive correlation between the occurrence of oncofetal glycan and tumor progression in various cancer types, the role of altered glycosylation in PCa has not been fully studied.

SUMMARY OF THE INVENTION

It is first demonstrated in the present invention that particular glycosyltransferase [core 1 beta-3-galactosyltransferase (C1GALT1) and ST3 beta-galactoside alpha-2,3-sialyltransferase 1 (ST3GAL1)] gene products and a galectin-4 gene product are highly correlated with progression of prostate cancer and therefore the glycosyltransferase gene products and the galectin-4 gene product and also the saccharide substrate used by the glycosyltransferases (e.g. UDP-GalNAc, UDP-Gal, CMP-sialic acid) and the saccharide product formed by the glycosyltransferases (i.e., sialyl-T-antigen) can be used as specific molecular markers for predicting prognosis and/or monitoring progression of prostate cancer.

Therefore, in one aspect, the present invention provides a method for predicting prognosis of prostate cancer, comprising
  (i) providing a biological sample from a subject afflicted with prostate cancer; and
  (ii) detecting a first marker and a second marker in the sample, wherein the first marker is a glycosyltransferase gene product and/or a saccharide substrate/product thereof, selected from the group consisting of core 1 beta-3-galactosyltransferase (C1GALT1), ST3 beta-galactoside alpha-2,3-sialyltransferase 1 (ST3GAL1), UDP-GalNAc, UDP-Gal, CMP-sialic acid, sialyl-T-anigen, and any combination thereof, and the second marker is a galectin-4 gene product.

In some embodiments, the gene product can be a protein or a RNA transcript.

In some embodiments, the first marker is detected with a first agent that that specifically binds to the glycosyltransferase or its saccharide substrate or product.

In some embodiments, the second marker is detected with a second agent that specifically binds to the galectin-4 gene product.

In some embodiments, the first agent is an antibody and/or the second agent is an antibody.

In particular, the detection is performed by a mass spectrometric assay or an immunoassay.

The biological sample to be examined in the methods described herein can be a body fluid sample or a tissue sample. Examples of a body fluid sample include but are not limited to semen, blood and urine.

In some embodiments, the method described herein can further comprise comparing the results of the detection with a reference level and predicting prognosis for the subject based on the results of the comparison. In some examples, presence of the marker(s) in the sample as compared to the absence of the marker(s) in a control sample (e.g., the reference value being 0) is indicative of a negative prognosis of prostate cancer. In other examples, an elevated level of the marker(s) is indicative of a negative prognosis.

In some embodiments, the negative prognosis is selected from the group consisting of a reduced survival rate, an increased tumor size or number, an increased risk of metastasis, an increased risk of resistance to androgen deprivation therapy (ADT), an increased risk of relapse, and any combination thereof.

In another aspect, the present invention provides a method for monitoring progression of prostate cancer in a patient afflicted with prostate cancer, comprising
(a) providing a first biological sample from the patient at a first time point;
(b) providing a second biological sample from the patient at a second time point, which is later than the first time point;
(c) detecting the levels of a first marker and a second marker in the first and second biological samples, wherein the first marker is a glycosyltransferase gene product and/or a saccharide substrate/product thereof, selected from the group consisting of core 1 beta-3-galactosyltransferase (C1GALT1), ST3 beta-galactoside alpha-2,3-sialyltransferase 1 (ST3GAL1), UDP-GalNAc, UDP-Gal, CMP-sialic acid, sialyl-T-anigen, and any combination thereof, and the second marker is a galectin-4 gene product; and
(d) determining prostate cancer progression in the patient based on the levels of the first marker and the second marker in the first and second biological samples, wherein an elevated level of the first marker and/or the second marker in the second biological sample as compared to that in the first biological sample is indicative of prostate cancer progression.

Also provided is a kit for performing the method as described herein, comprising a first reagent that specifically recognizes the first marker and a second reagent that specifically recognizes the second marker, and instructions for using the kit to detect the presence or amount of the first biomarker and/or the second biomarker.

Further provided is a use of a reagent that specifically recognizes the biomarker(s) as described herein for predicting prognosis of prostate cancer or a method for monitoring progression of progression of prostate cancer, or in the manufacture of a kit or a composition for performing a method for predicting prognosis of prostate cancer or a method for monitoring progression of progression of prostate cancer.

In some embodiments, the reagent is selected from the group consisting (i) a molecule that specifically recognizes C1GALT1, (ii) a molecule that specifically recognizes ST3GAL1, (iii) a molecule that specifically recognizes UDP-GalNAc, (iv) a molecule that specifically recognizes UDP-Gal, (v) a molecule that specifically recognizes CMP-sialic acid, (vi) a molecule that specifically recognizes sialyl-T-anigen, (vii) a molecule that specifically recognizes galectin-4 gene product, and (viii) any combination of (i) to (vii).

The details of one or more embodiments of the invention are set forth in the description below. Other features or advantages of the present invention will be apparent from the following detailed description of several embodiments, and also from the appending claims

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A shows that the C1GALT1 expression level in the published PCa cohort from GSE32269 (Left) and GSE35988 (Right). ***$P<0.001$ (unpaired t-test, two-tail). FIG. 1B shows that expression of C1GALT1 in a commercial PCa tissue array was determined using IHC and analyzed for pathological stages by chi-square test, $P=0.0027$. Right, representative IHC images of normal prostate tissue and stage IV of PCa.

FIG. 2A shows the flow-chart of in vivo CRPC development from LNCaP cells. Below, longitudinal BLI (bioluminescence imaging) of LNCaP-derived orthotopic tumors was quantitatively analyzed for tumor growth curve and value are expressed as mean±SEM, n=5. FIG. 2B shows the representative colony-formation assays and quantifications of LNCaP and LNCaP-CR4 cells under enzalutamide treatment for 10 days. FIG. 2C shows immunoblots of C1GALT1 in LNCaP cells and their derivatives. FIG. 2D shows quantitative RT-PCR of C1GALT1 for LNCaP and LNCaP-derived CRPC cells. FIG. 2E shows schematic drawing of lectin binding sites in N-glycans and mucin-type O-glycans. FIG. 2F shows that the surface glycophenotype of LNCaP and LNCaP-CR4 cells were analyzed using PNA, jacalin, and PHA-L lectins staining. Below, the mean fluorescence intensity (MFI) values from triplicates. FIG. 2G shows the immunoblots of C1GALT1, androgen receptor (AR), PSA, and cleavage PARP (cl. PARP) in CR4-shCtrl and CR4-shC1GALT1 cells grown in CD-FBS medium with or without 1 nmol/L DHT for 4 days. FIG. 2H shows the cell viability assay of LNCaP-CR4 cells with knockdown of control (CR-shCtrl) or C1GALT1 (CR4-shC1GALT1 #1, #2) shRNAs. Cells were grown in CD-FBS medium (ADT) with or without DHT supplement for 6 days. Data are normalized to values at day 0. FIG. 2I shows the quantitative RT-PCR of galectin-4, PSA, and AR in CR4-shCtrl and CR4-shC1GALT1. Data are expressed as mean±SEM. *$P<0.05$, $P<0.01$, *$P<0.001$ (unpaired t-test, two-tail).

FIG. 3A shows the quantitative RT-PCR of galectin-1, 2, 3, 4, 8, and 9 for LNCaP and LNCaP-derived CRPC cells. FIG. 3B shows the cell viability assay of LNCaP-CR4 cells stably expressing control (CR4-shCtrl) or galectin-4 (CR4-shGal4 #1, #2) shRNAs. Cells were grown in CD-FBS medium (ADT) with or without DHT supplement for 6 days. Data are normalized to values at day 0. FIG. 3C shows the immunoblots of galectin-4 and cleavage PARP (cl. PARP) in CR4-shCtrl and CR4-shGal4 grown in CD-FBS medium with or without 1 nmol/L DHT for 4 days. FIG. 3D shows the quantitative RT-PCR of galectin-4, androgen receptor (AR), and PSA in LNCaP-CR4 cells stably expressing control (CR-shCtrl) or galectin-4 (CR4-shGal4 #1, #2) shR-NAs. FIG. 3E shows the immunoblots of galectin-4, HER2/3 phosphorylation, AR, and PSA expression in LNCaP-tetO-Gal4 and 22Rv1-tetO-Gal4 cells treated with 3 μM Swainsonine or 4 mM Benzyl-α-GalNAc for 2 day following doxycycline-mediated galectin-4 induction. FIG. 3F shows the surface glycophenotype of 22Rv1 and 22Rv1-M4 cells were analyzed using jacalin and galectin-4 staining. Below, the mean fluorescence intensity (MFI) values from triplicates. FIG. 3G shows the representative colony formation assay and quantifications of M4-shCtrl, M4-shGal4, and M4-shC1GALT1 cells grown for 10 days. Data are expressed as mean±SEM. *P<0.05, P<0.01, *P<0.001 (unpaired t-test, two-tail).

FIG. 4A shows that the longitudinal BLI of CR4-shCtrl or CR4-shGal4 tumors were determined for tumor growth as FIG. 2A. $2 \times 10^5$ of cells were implanted in the prostate of NOD-SCID mice with or w/o castration, n=6. FIG. 4B shows that the tumor weights from 4A at the endpoint are presented as mean±SEM (n=6). Right, gross appearance of tumors. FIG. 4C shows that BLI of lymph nodes from 4A were examined at the endpoint. Right, representative BLI images. FIG. 4D shows the longitudinal BLI of LNCaP orthotopic tumors expressing tetracycline-inducible galectin-4 in nude mice, n=6. DOX was added to drinking water (0.5 mg/mL) and refreshed every three days. FIG. 4E shows the IHC staining of galectin-4 in different groups as indicated. FIG. 4F show the column scatter plot presents the BLI of lymph nodes at the endpoint, n=6. Right, representative BLI images and staining of anti-CK18 antibody in the metastases. Data are presented as mean±SEM. *P<0.05, P<0.01, *P<0.001 (unpaired t-test, two-tail).

FIG. 5A to FIG. 5F show that galectin-4-mediated SOX9 expression promotes stem-like phenotype and metastatic colonization. FIG. 5A shows GSEA revealing that the transcriptomic footprint of galectin-4 is significantly enriched for genes in HER2 signaling, cancer stem cells, and the O-glycan biosynthesis pathway in M4-shCtrl compared to M4-shGal4. The differentially expressed genes ($P_{adj}$<0.05 and FC≥1.5) were identified by whole genome microarray comparing shRNA-mediated galectin-4 knockdown in M4 cells or forced galectin-4 expression in LNCaP and 22Rv1 cells. FIG. 5B shows the representative tumorsphere assay and quantification of M4-shCtrl or M4-shGal4 cells. FIG. 5C shows the effect of SOX9 expression on tumorsphere formation. Representative tumorsphere assay and quantification for 22Rv1-M4 cells stably transfected with control or SOX9 shRNAs and induction for 10 days. FIG. 5D shows the metastatic colonization assay by tail vein injection of $1 \times 10^6$ of M4-shCtrl or M4-shSOX9 cells into NOD-SCID mice, n=8. Below, the representative BLI images from indicated groups. FIG. 5E shows the immunoblots of C1GALT1, galectin-4 (Gal4), SOX9, and ALDH1A1 in M4-shC1GALT1 and M4-shCtrl cells. FIG. 5F shows the representative tumorsphere assay and quantification of M4-shCtrl and M4-shC1GALT1 cells. Data are presented as mean±SEM. *P<0.05, P<0.01, *P<0.001 (unpaired t-test, two-tail).

FIG. 6A to FIG. 6J show that galectin-4 expression regulates the MYC-mediated O-glycosylation biosynthetic pathway. FIG. 6A shows qRT-PCR of galectin-4 (Gal4), C1GALT1, GCNT1, and ST3GAL1 in 22Rv1-M4 cells expressing control or galectin-4 shRNAs. FIG. 6B shows prediction of transcription factors enriched in galectin-4-mediated gene signatures from LNCaP cells using the ENCODE TF ChIP-seq database. FIG. 6C shows qRT-PCR of core 1 O-glycan-related enzymes and MYC in 22Rv1-M4 cells expressing control (M4-shCtrl) or MYC (M4-shMYC #1, #2) shRNAs. FIG. 6D) The expression level of MYC, C1GALT1, SOX9, and galectin-4 in 22Rv1-M4 cells expressing control or MYC shRNAs. FIG. 6E shows glycophenotypes of M4-shCtrl and M4-shMYC cells were analyzed using jacalin, PHA-L, and galectin-4 staining. Below, the mean fluorescence intensity (MFI) values from triplicates. FIG. 6F shows representative tumorsphere images and quantification of tumorsphere assay of M4-shCtrl and M4-shMYC cells. FIG. 6G shows galectin-4 binding assay for 22Rv1-tetO-MYC and LNCaP-tetO-MYC with or without DOX treatment for 4 days. Below, the mean fluorescence intensity (MFI) values from triplicates. FIG. 6H shows immunoprecipitation of HER2 in LNCaP-CR4 cells followed by jacalin and galectin-4 lectin blotting. FIG. 6I shows ChIP-qPCR of MYC binding to the promoter regions of C1GALT1 in 22Rv1-M4. Neg Ctrl, negative control primers were designed for the regions approximately 2000 bp upstream of the MYC binding site in the C1GALT1 promoter. FIG. 6J shows pearson correlation analysis for expression level between C1GALT1 and MYC activity score in published PCa cohort from GSE21032. Except for 6J, data are presented as mean±SEM. *P<0.05, P<0.01, *P<0.001 (unpaired t-test, two-tail).

FIG. 7A to FIG. 7G show that C1GALT1 upregulation correlated with clinical stages and increased risk of galectin-4 in PCa. FIG. 7A shows that the mRNA levels of galectin-4 and C1GALT1 were determined in PCa and paired adjacent normal tissues, n=21. The P value was determined by paired t-test. FIG. 7B shows that the correlation between galectin-4 and C1GALT1 mRNA levels from 7A was analyzed using Pearson's correlation coefficient. FIG. 7C shows the pearson correlation analysis for expression level between C1GALT1 and galectin-4 in a published PCa cohort from GSE32269. FIG. 7D shows the forest plot comparison of the hazard ratio (HR) of galectin-4 and C1GALT1 overexpression in clinical PCa, n=231. HR and P value were determined by Log-rank test. FIG. 7E shows the Kaplan-Meier survival analysis in indicated subgroups as in FIG. 7D. FIG. 7F shows the representative IHC images from FIG. 7E. FIG. 7G shows the Pearson correlation analysis for staining scores between galectin-4 and C1GALT1 from 7E.

FIG. 8A and FIG. 8B show lectin binding assay of LNCaP-tetO-Gal4 (A) and 22Rv1-tetO-Gal4 (B) cells treated with 3 µM Swainsonine or 4 mM Benzyl-α-GalNAc for 2 day following galectin-4 induction by doxycycline. FIG. 8C shows that the surface glycophenotype of 22Rv1 and 22Rv1-M4 cells were analyzed using PNA and PHA-L lectin staining. Below, the mean fluorescence intensity (MFI) values from triplicates. Data are expressed as mean±SEM. *P<0.05, P<0.01, *P<0.001 (unpaired t-test, two-tail).

FIG. 9A shows qRT-PCR of galectin-4 and SOX9 in 22Rv1-M4 cells expressing control (M4-shCtrl) or galectin-4 (M4-shGal4 #1, #2) shRNAs. FIG. 9B shows the effect of SOX9 expression on tumorsphere formation. Representative tumorsphere assay and quantification for LNCaP-CR4 cells stably transfected with control (CR4-shCtrl) or SOX9 (CR4-shSOX9 #1, #2) shRNAs. FIG. 9C shows the lectin binding assay of 22Rv1-M4 cells treated with 3 µM Swainsonine or 4 mM Benzyl-α-GalNAc for 2 day. FIG. 9D shows the immunoblots of galectin-4-mediated RTK phosphorylation and SOX9 expression in 22Rv1-M4 cells following 3 µM Swainsonine or 4 mM Benzyl-α-GalNAc (Bn-α-GalNAc) treatment for 2 days. FIG. 9E shows the immunoblots of galectin-4 (Gal4), SOX9, and ALDH1A1 in LNCaP and PC-3 cells stably transfected with tetracycline-inducible galectin-4 in the presence or absence of doxycycline for 4 days. FIG. 9F shows the representative tumor sphere assays and quantification of LNCaP-tetO-Gal4 and PC-3-tetO-Gal4 cells with or without doxycycline over 3 serial passages. Data are expressed as mean±SEM. ***P<0.001 (unpaired t-test, two-tail).

Figure 10A:
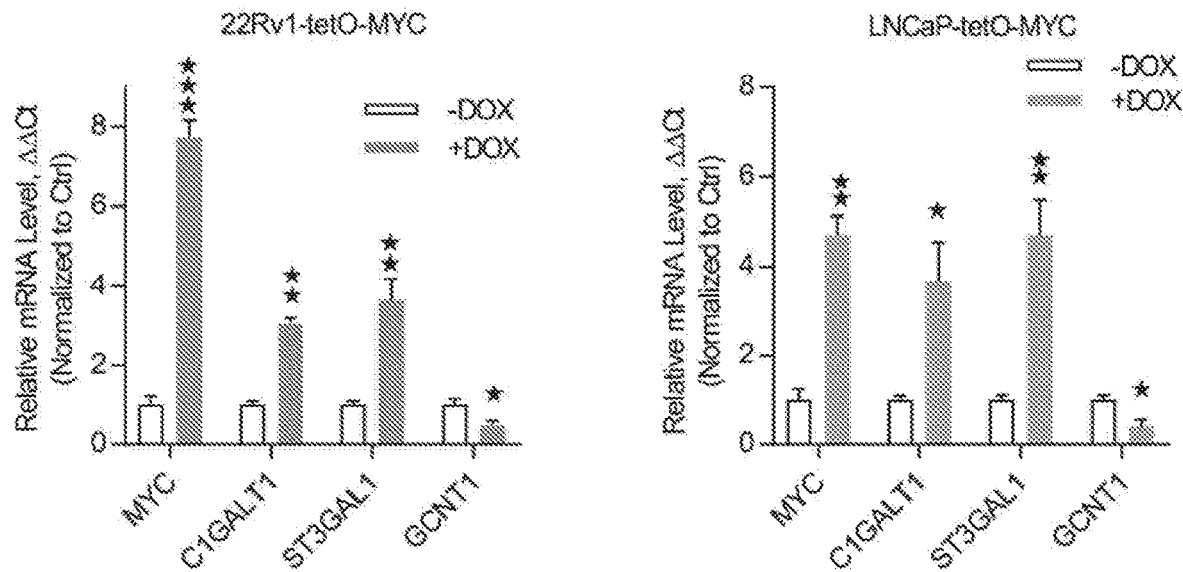
Figure 10B:
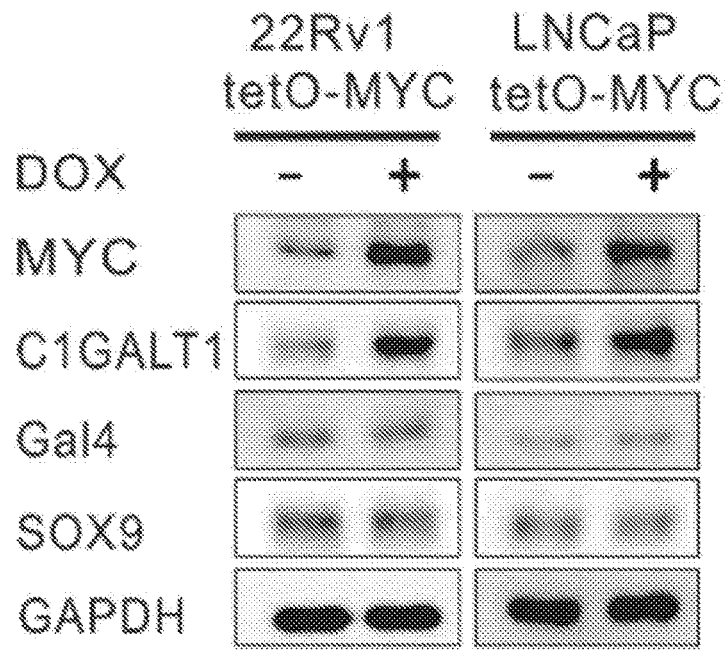
Figure 10C:
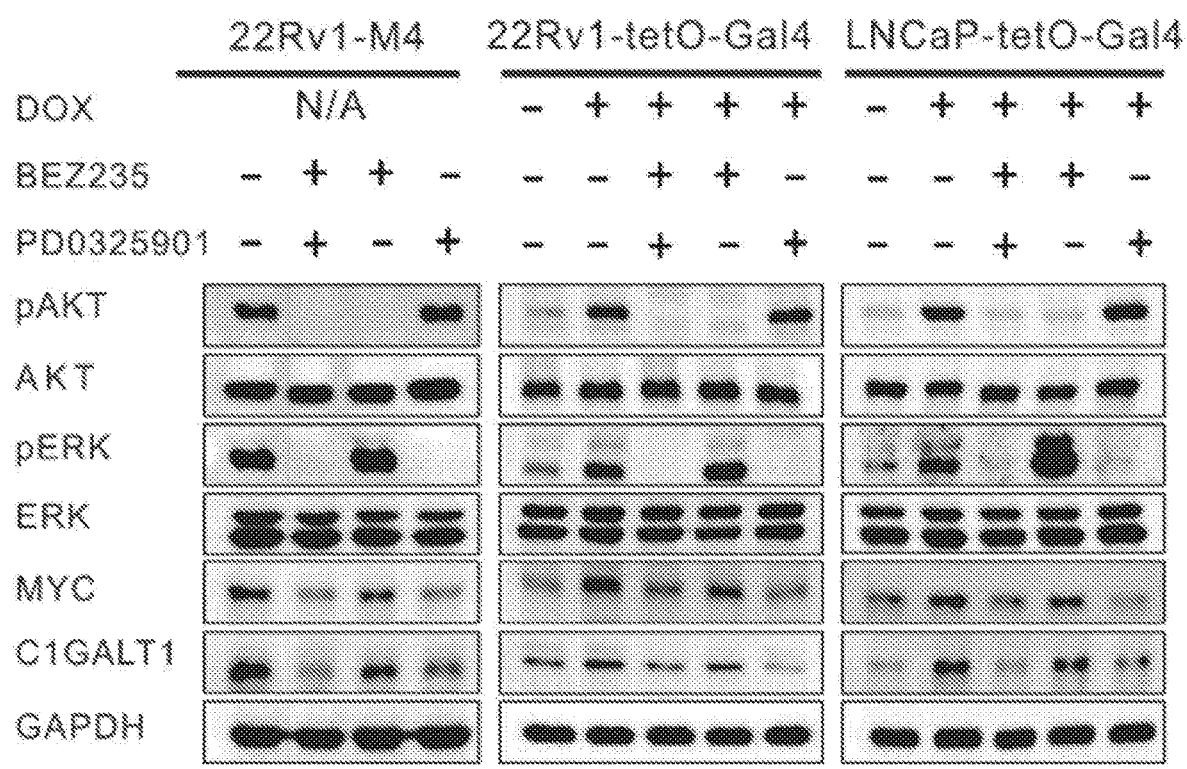

FIG. 10A to FIG. 10C show that the MYC expression regulates gene signatures for O-glycosylation. FIG. 10A shows qRT-PCR of MYC and core 1 O-glycan-related glycosyltransferase in 22Rv1-tetO-MYC (Left) and LNCaP-tetO-MYC (Right) cells with or without DOX treatment for 4 days. FIG. 10B shows the immunoblots of MYC, C1GALT1, galectin-4 (Gal4), and SOX9 in 22Rv1-tetO-MYC and LNCaP-tetO-MYC cells with or without doxycycline treatment for 4 days. FIG. 10C shows the immunoblots of AKT and ERK phosphorylation, MYC, and C1GALT1 levels in 22Rv1-M4 cells and galectin-4-expressing 22Rv1 and LNCaP cells under the indicated treatments for 24 h. Data are expressed as mean±SEM. *P<0.05, P<0.01, *P<0.001 (unpaired t-test, two-tail).

DETAILED DESCRIPTION OF THE INVENTION

Disseminated castration-resistant prostate cancer (CRPC) is a common disease in men characterized by limited survival and resistance to androgen deprivation therapy (ADT). The increase in HER2 signaling contributes to androgen receptor (AR) activity in a subset of CRPC patients; however, enigmatically, HER2-targeted therapies show a lack of efficacy in CRPC patients. Aberrant glycosylation is a hallmark of cancer and involves the key processes that support cancer progression. Using transcriptomic analysis of PCa datasets, histopathological examination of clinical specimens, and in vivo experiments of xenograft models, in this study, we revealed a coordinated increase in glycan-binding protein galectin-4, specific glycosyltransferases (C1GALT1 and ST3GAL1), and the resulting mucin-type O-glycans during the progression of CRPC. Furthermore, galectin-4 engaged with C1GALT1-dependent O-glycans to promote castration resistance and metastasis by activating RTK signaling and cancer cell stemness properties mediated by SOX9. This galectin-glycan interaction upregulated MYC-dependent expression of C1GALT1 and ST3GAL1, which altered the cellular mucin-type O-glycosylation to allow galectin-4 binding. In clinical PCa, high-level expression of C1GALT1 and galectin-4 together predict poor overall survival compared to low-level expression of C1GALT1 and galectin-4. In conclusion, MYC regulates abnormal O-glycosylation thus priming cells for binding to galectin-4 and downstream signaling, which promotes castration resistance and metastasis.

It is disclosed in the present invention that particular glycosyltransferase [core 1 beta-3-galactosyltransferase (C1GALT1) and ST3 beta-galactoside alpha-2,3-sialyltransferase 1 (ST3GAL1)] gene products and/or their saccharide substrates used by the glycosyltransferases (including UDP-GalNAc, UDP-Gal, CMP-sialic acid) and the saccharide product formed by the glycosyltransferases (i.e. sialyl-T-antigen) can be used as specific molecular markers for predicting prognosis and/or monitoring progression of prostate cancer.

The following description is merely intended to illustrate various embodiments of the invention. As such, specific embodiments or modifications discussed herein are not to be construed as limitations to the scope of the invention. It will be apparent to one skilled in the art that various changes or equivalents may be made without departing from the scope of the invention.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

As used herein, the term "about" or "approximately" refers to a degree of acceptable deviation that will be understood by persons of ordinary skill in the art, which may vary to some extent depending on the context in which it is used. In general, "about" or "approximately" may mean a numeric value having a range of ±10% around the cited value.

As used herein, the term "nucleic acid fragment," "nucleic acid" and "polynucleotide," used interchangeably herein, refer to a polymer composed of nucleotide units, including naturally occurring nucleic acids, such as deoxyribonucleic acid ("DNA") and ribonucleic acid ("RNA") as well as nucleic acid analogs including those which have non-naturally occurring nucleotides. Thus, these terms include, but are not limited to, single-, double-, or multi-stranded DNA or RNA, genomic DNA, cDNA, mRNA, DNA-RNA hybrids, or a polymer comprising purine and pyrimidine bases or other natural, chemically or biochemically modified, non-natural, or derivatized nucleotide bases. It will be understood that when a nucleic acid fragment is represented by a DNA sequence (i.e., A, T, G, C), this also includes an RNA sequence (i.e., A, U, G, C) in which "U" replaces "T."

As used herein, the term "primer" as used herein refers to a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase. For example, primers for C1GALTs and galectin-4, as used herein, respectively, are those which are capable to hybridize to the nucleotide sequence of the individual target genes to initiate nucleotide polymerization and produce the nucleotide products as expected based on the design of the sequences of the primers.

As used herein, the term "probe" as used herein refers to a defined nucleic acid segment (or nucleotide analog segment, e.g., polynucleotide as defined herein) which can be used to identify a specific polynucleotide sequence present in samples during hybridization, said nucleic acid segment comprising a nucleotide sequence complementary of the specific polynucleotide sequence to be identified. Typically, a probe can produce a detectable signal since it is labeled in some way, for example, by incorporation of a reporter molecule such as a fluorophore or radionuclide or an enzyme. For example, probes for C1GALTs and galectin-4, as used herein, respectively, are those which are capable to specifically hybridize to the corresponding nucleotide sequence of the individual target genes and produce detectable signals caused by such hybridization.

As used herein, the term "hybridization" as used herein shall include any process by which a strand of nucleic acid joins with a complementary strand through base pairing. Relevant technologies are well known in the art and described in, for example, Sambrook et al., Molecular Cloning: A Laboratory Manual, $2^{nd}$ ed., Cold Spring Harbor Laboratory Press (1989), and Frederick M. A. et al., Current Protocols in Molecular Biology, John Wiley & Sons, Inc.

(2001). Typically, stringent conditions are selected to be about 5 to 30° C. lower than the thermal melting point (Tm) for the specified sequence at a defined ionic strength and pH. More typically, stringent conditions are selected to be about 5 to 15° C. lower than the T m for the specified sequence at a defined ionic strength and pH. For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). An exemplary non-stringent or low stringency condition for a long probe (e.g., greater than 50 nucleotides) would comprise a buffer of 20 mM Tris, pH 8.5, 50 mM KCl, and 2 mM $MgCl_2$, and a reaction temperature of 25° C.

As used herein, the term "encode" as used herein refers to the inherent property of specific sequences of nucleotides in a polynucleotide (e.g., a gene, a cDNA, or an mRNA) to serve as templates for synthesis of a gene product having either a defined sequence of nucleotides (i.e., rRNA, RNA and mRNA) or a defined sequence of amino acids and the biological properties resulting therefrom.

As used herein, the term "expression" as used herein refers to the realization of genetic information encoded in a gene to produce a gene product such as an unspliced RNA, an mRNA, a splice variant mRNA, a polypeptide or protein, a post-translationaly modified polypeptide, a splice variant polypeptide and so on.

As used herein, the term "expression level" refers to the amount of a gene product expressed by a particular gene in cells which can be determined by any suitable method known in the art.

As used herein, the terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones.

As used herein, the term "antibody" means an immunoglobulin protein which is capable of binding an antigen. Antibody as used herein is meant to include the entire antibody as well as any antibody fragments (e.g., F (ab') .sub.2, Fab', Fab, Fv) capable of binding the epitope, antigen, or antigenic fragment of interest. Antibodies of the invention are immunoreactive or immunospecific for and therefore specifically and selectively bind to a protein of interest, e.g., C1GALTs and galectin-4. Antibodies for the proteins of interest are preferably immunospecific, i.e., not substantially cross-reactive with related materials, although they may recognize their homologs across species. The term "antibody" encompasses all types of antibodies (e.g., monoclonal and polyclonal).

As used herein, a biological marker (or called biomarker or marker) is a characteristic that is objectively measured and evaluated as an indicator of normal or abnormal biologic processes/conditions, diseases, pathogenic processes, or responses to treatment or therapeutic interventions. Markers can include presence or absence of characteristics or patterns or collections of the characteristics which are indicative of particular biological processes/conditions. A marker is normally used for diagnostic and prognostic purposes. However, it may be used for therapeutic, monitoring, drug screening and other purposes described herein, including evaluation the effectiveness of a cancer therapeutic.

As used herein, a biological sample to be analyzed by any of the methods described herein can be of any type of samples obtained from a subject to be detected. In some embodiments, a biological sample can be a body fluid sample such as a blood sample, a urine sample, an ascetic sample or a semen sample. Typically, a biological sample is a urine sample. In other embodiments, a blood sample can be whole blood or a faction thereof e.g. serum or plasma, heparinized or EDTA treated to avoid blood clotting. Alternatively, the biological sample can be a tissue sample or a biopsy sample from tumor.

As used herein, the terms "subject," "individual" and "patient," used interchangeably herein, refer to a mammalian subject for whom diagnosis, prognosis, treatment, or therapy is needed, particularly humans. Other subjects may include cattle, dogs, cats, guinea pigs, rabbits, rats, mice, horses, and so on.

As used herein, the term "diagnosis" as used herein generally includes determination as to whether a subject is likely affected by a given disease, disorder or dysfunction. The skilled artisan often makes a diagnosis on the basis of one or more diagnostic indicators, i.e., a marker, the presence, absence, or amount of which is indicative of the presence or absence of the disease, disorder or dysfunction. It will be understood in the art that diagnosis does not mean determining the presence or absence of a particular disease with 100% accuracy, but rather an increased likelihood of the presence of certain disease in a subject.

As used herein, the term "prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. It would be understandable that a positive prognosis typically refers to a beneficial clinical outcome or outlook, such as long-term survival without recurrence of the subject's cancerous conditions, whereas a negative prognosis typically refers to a negative clinical outcome or outlook, such as cancer recurrence or progression. In certain embodiments, the negative prognosis is selected from the group consisting of a reduced survival rate, an increased tumor size or number, an increased risk of metastasis, an increased risk of resistance to androgen deprivation therapy (ADT), an increased risk of relapse, and any combination thereof.

As used herein, the term "treatment" refers to the application or administration of one or more active agents to a subject afflicted with a disorder, a symptom or condition of the disorder, or a progression of the disorder, with the purpose to cure, heal, alleviate, relieve, alter, remedy, ameliorate, improve, or affect the disorder, the symptom or condition of the disorder, the disabilities induced by the disorder, or the progression or predisposition of the disorder.

As used herein, the term "normal individual" may be used interchangeably to refer to an individual who is healthy and does not suffer from the disease (e.g., prostate cancer), and may refer to a single normal individual or a group of normal individuals.

As used herein, an "aberrant level" can refer to a level that is increased compared with a reference level. For example, an aberrant level can be higher than a reference level by more than 10%, 20%, 30%, 40%, 50%, 60%, 70%, 80%, 90% or 100%. In some embodiments, the expression level of a biomarker as described herein in a subject to be tested is compared to a standard level based on historical values. For example, the standard level can be set based on an average or median expression level of such biomarker in corresponding biological samples obtained from a cohort of subjects. For instance, the cohort of subjects can be a group of prostate cancer patients enrolled in a clinical trial. In particular embodiments, the cohort of subjects can be a group of prostate cancer patients in primary/early stage of disease without progression e.g. metastasis or resistance to androgen deprivation therapy (ADT). In some embodiments, a reference level can refer to the level measured in normal individuals or samples such as tissues or cells that are not diseased (adjacent non-cancerous/normal tissues).

As used herein, "low expression" and "high expression" for a biomarker as used herein are relative terms that refer to the level of the biomarker found in a sample. In some embodiments, low and high expression can then be assigned to each sample based on whether the expression of such biomarker in a sample is above (high) or below (low) the average or median expression level. In some embodiments, low and high expression can be determined by comparison of the biomarker expression level in a non-cancerous sample, where low expression can refer to a lower or comparable expression level to the expression level in a non-cancerous sample, and high expression can refer to a higher expression level to the expression level in a non-cancerous sample.

As used herein, Galectin-4 is a protein that in humans is encoded by the LGALS4 gene. Core 1 beta-3-galactosyl-transferase (C1GALT1) is an enzyme which in humans is encoded by the C1GALT1 gene. ST3 beta-galactoside alpha-2,3-sialyltransferase 1 (ST3GAL1) is an enzyme which in humans is encoded by the ST3GAL1 gene. The nucleotide sequences of the biomarker genes as described above and the corresponding amino acid sequences of their gene products are well known in the art. Galectin-4 or LGALS4 NCBI Gene ID: 3960. Its external links ID: HGNC: 6565. Entrez Gene: 3960. Ensembl: ENSG00000171747. OMIM: 602518. UniProtKB: P56470. C1GALT1 ID: HGNC: 24337. Entrez Gene: 56913. Ensembl: ENSG00000106392. OMIM: 610555, UniProtKB: Q9NS00. ST3GAL1 ID: HGNC: 10862. Entrez. Gene: 6482. Ensembl: ENSG00000008513. OMIM: 607187. UniProtKB: Q11201.

To perform the methods described herein, a biological sample can be obtained from a subject in need and the first marker and/or the second marker in the biological sample can be detected or measured via any methods known in the art, such as mass spectrometry and immunoassays. A biological sample can be a biofluid sample, such as semen, blood and urine. The detection of the marker(s) may be quantitative or qualitative. In one embodiment, a sample obtained from a subject in need is analyzed for the presence or absence of the marker(s). If the marker(s) is detected in a sample obtained from a subject in need, the subject is identified as having a negative prognosis of prostate cancer. In some embodiments, the level of the marker(s) in a sample obtained from a candidate subject can be compared with a reference level to determine whether the candidate subject has a negative prognosis of prostate cancer. A higher level of the marker(s) as detected in a biological sample from the candidate subject can indicate that the candidate subject has a negative prognosis of prostate cancer. In some examples, the level of the marker(s) in a control sample is undetectable in a control sample (i.e. the reference value being 0) using a routine assay e.g. mass spectrometry and immunoassays, and the presence of the marker as detected in a biological sample from a subject using the same assay can indicate that the subject has a negative prognosis of prostate cancer. In some examples, the level of the marker(s) can be measured at different time points in order to monitor the progression of the prostate cancer. For example, two biological samples are obtained from a candidate subject at two different time points. If a trend of increase in the level of the marker(s) is observed over time, for example, the level of the marker(s) in a later obtained sample is higher than that in an earlier obtained sample, the subject is deemed as having a negative prognosis of prostate cancer.

The presence and amount of the biomarker as described herein in a biological sample can be determined by routine technology. In some embodiments, the presence and/or amount of the biomarker as described herein can be determined by mass spectrometry, which allows direct measurements of the analytes with high sensitivity and reproducibility. A number of mass spectrometric methods are available. Examples of mass spectrometry include, but are not limited to, liquid chromatography-mass spectrometry (LC-MS), liquid chromatography tandem mass spectrometry (LC-MS-MS), electrospray ionization mass spectrometry (ESI-MS), matrix-assisted laser desorption ionization/time of flight (MALDI-TOF), and surface-enhanced laser desorption ionisation/time of flight (SELDI-TOF). One certain example of this approach is tandem mass spectrometry (MS/MS), which involves multiple steps of mass selection or analysis, usually separated by some form of fragmentation.

In other embodiments, the presence and/or amount of a biomarker can be determined by an immunoassay. Examples of the immunoassays include, but are not limited to, Western blot, enzyme-linked immunosorbent assay (ELISA), radio-immunoassay (RIA), radioimmunoprecipitation assay (RIPA), immunofluorescence assay (IFA), ELFA (enzyme-linked fluorescent immunoassay), electrochemiluminescence (ECL), and Capillary gel electrophoresis (CGE). In some examples, the presence and/or level of a biomarker can be determined using an agent specifically recognizes said biomarker, such as an antibody that specifically binds to the biomarker.

In other embodiments, the presence and/or amount of a biomarker can be determined by measuring mRNA levels of the one or more genes. Assays based on the use of primers or probes that specifically recognize the nucleotide sequences of the genes as described may be used for the measurement, which include but are not limited to reverse transferase-polymerase chain reaction (RT-PCR) and in situ hybridization (ISH), the procedures of which are well known in the art. Primers or probes can readily be designed and synthesized by one of skill in the art based on the nucleic acid region of interest. It will be appreciated that suitable primers or probes to be used in the invention can be designed using any suitable method in view of the nucleotide sequences of the genes of interest as disclosed in the art.

Antibodies as used herein may be polyclonal or monoclonal. Polyclonal antibodies directed against a particular protein are prepared by injection of a suitable laboratory animal with an effective amount of the peptide or antigenic component, collecting serum from the animal, and isolating specific sera by any of the known immunoadsorbent techniques. Animals which can readily be used for producing polyclonal antibodies as used in the invention include chickens, mice, rabbits, rats, goats, horses and the like.

In some embodiments, the amount of a biomarker in the sample derived from the candidate individual can be compared to a standard value to determine whether the candidate individual has a negative prognosis of prostate cancer. The standard value may represent the average or median amount of a biomarker as described herein in a population of prostate cancer patients. Typically, such population of prostate cancer patients are chosen to be matched to the candidate individual in, for example, age and/or ethnic background. Preferably, such population of prostate cancer patients and the candidate individual are of the same species.

When an individual, such as a human patient, is diagnosed as having a negative prognosis, the individual may undergo further testing (e.g., routine physical testing, including surgical biopsy or imaging methods, such as X-ray imaging, magnetic resonance imaging (MRI), or ultrasound) to confirm the occurrence of the disease and/or to determine the stage and progression of cancer.

In some embodiments, the methods described herein can further comprise treating the prostate cancer patient to at least relieve symptoms associated with the disease. The treatment can be any conventional anti-prostate cancer therapy, including radiation therapy, chemotherapy, and surgery.

Also provided is a kit for performing the method of the invention. Specifically, the kit comprises a reagent (e.g., an antibody, a primer, a probe, or a labeling reagent) that can specifically detect the marker(s) as described herein. The kit can further instructions for using the kit to detect the presence or amount of the marker(s) in a biological sample for predicting prognosis and/or monitoring progression of prostate cancer. The components including the detection reagents as described herein can be packaged together in the form of a kit. For example, the detection reagents can be packaged in separate containers, e.g., a nucleic acid (a primer or a probe) or antibody (either bound to a solid matrix or packaged separately with reagents for binding them to the matrix), a control reagent (positive and/or negative), and/or a detectable label, and the instructions (e.g., written, tape, VCR, CD-ROM, etc.) for performing the assay can also be included in the kit. The assay format of the kit can be a Northern hybridization, a chip or an ELISA, for example. Further provided is use of such reagent for performing a method for predicting prognosis and/or monitoring progression of prostate cancer. Such reagent includes a first reagent that specifically recognizes the first biomarker, and/or a second reagent that specifically recognizes the second biomarker. In some embodiments, such reagent includes a first reagent that is selected from the group consisting of (i) a molecule that specifically recognizes C1GALT1, (ii) a molecule that specifically recognizes ST3GAL1, (iii) a molecule that specifically recognizes UDP-GalNAc, (iv) a molecule that specifically recognizes UDP-Gal, (v) a molecule that specifically recognizes CMP-sialic acid, (vi) a molecule that specifically recognizes sialyl-T-antigen, (vii) a molecule that specifically recognizes galectin-4 gene product, and (viii) any combination of (i) to (vii). In some embodiments, such reagent includes a second reagent that specifically recognizes galectin-4. Examples of the reagent can be an antibody, a primer, a probe, or a labeling reagent containing a detectable label (e.g. a fluorescent label) that can specifically recognize a biomarker. The reagent may be mixed with a carrier e.g. a pharmaceutically acceptable carrier to form a composition for the detection or diagnosis purpose. Examples of such carrier include injectable saline, injectable distilled water, an injectable buffer solution and the like.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

We investigated the regulation of tumor-associated glycosylation genes to identify potential treatments tailored to a specific subgroup of CRPC. In this study, a transcriptomic dataset and pathological examination revealed the high expression of C1GALT1 and ST3GAL1 among glycosylation genes associated with mCRPC over primary PCa. Consistently, in vivo tumor progression from orthotopic xenografts of both LNCaP and 22Rv1 cells exhibited a concomitant increase in specific mucin-type O-glycosyltransferases that synthesize core 1 O-glycans, including C1GALT1 and ST3GAL1. Importantly, we further found that C1GALT1 mediates O-glycosylation encoding for galectin-4 binding and signaling which promotes castration resistance, cancer cell stemness properties, and metastasis. Further, the co-expression of C1GALT1 and galectin-4 in clinical specimens exhibited synergistic interaction that correlated with poor overall survival.

Abbreviations:

ADT, androgen deprivation therapy; AR, androgen receptor; BLI, bioluminescence imaging, ChIP, chromatin immunoprecipitation; cl. PARP, cleavage Poly (ADP-ribose) polymerase; CSCs, cancer stem cells; CRPC, castration-resistant prostate cancer; DHT, dihydrotestosterone; GSEA, Gene Set Enrichment Analysis; IHC, immunohistochemistry; PCa, prostate cancer; MSigDB, Molecular Signatures Database; PNA, Peanut Agglutinin lectin; PHA-L, *Phaseolus Vulgaris* Leucoagglutinin; qPCR, quantitative PCR.

1. Material and Methods 1.1 Chemical Reagents and Antibodies

Commercial antibodies against galectin-4 (GeneTex, Hsinchu City, Taiwan), pHER2 (EMD Millipore, Billerica, MA), C1GALT1 for IHC (Sigma-Aldrich, St. Louis, MO), ERK, C1GALT1, androgen receptor (Santa Cruz Biotechnology, Dallas, TX), pIGF1R, pHER3, and GAPDH (Abcam, San Francisco, CA) were used. The other antibodies were from Cell Signaling Technology, Danvers, MA. Biotinylated lectins were from Vector Labs (Burlingame, CA). Inhibitors, lapatinib, linsitinib, BEZ235, and PD0325901, were from AdooQ BioScience (Irvine, CA). Swainsonine and benzyl-α-GalNAc were purchased from EMD Millipore.

1.2 Cell Lines

22Rv1, LNCaP, and PC-3 cell lines were obtained from the American Type Culture Collection (ATCC, Manassas, VA). The authentication of cell lines and their derivatives was performed by analyzing STR profiles and comparing in the ATCC database within six months. All cell lines were routinely cultured in RPMI-1640 supplemented with 2 mM glutamine, 1 mM sodium pyruvate, and 10% fetal bovine serum.

1.3 Quantitative RT-PCR

For induction of galectin-4, cells were treated with doxycycline (DOX, 1 µg/mL) for 4 days. Total RNA was isolated using TRIzol reagent (Invitrogen), and complementary DNA was synthesized from equivalent concentrations of total RNA using PrimeScript RT Reagent Kit (TaKaRa) in accordance with manufacturer's instructions. The coding sequence for genes of interest as well as a loading control (GAPDH) was amplified using Bio-rad SYBR Green Supermix and carried out using a Bio-rad CFX real-time PCR system. Cycle threshold values were determined and normalized to the loading control for each experiment and values are presented as fold change relative to respective controls ($2^{-\Delta\Delta Ct}$). The PCR amplifications were carried out using specific primers for each gene as follows: C1GALT1 forward primer
(SEQ ID NO: 1)
5'-TCCCTTTGTGCCAGAACACC, reverse primer
(SEQ ID NO: 2)
5'-AGCAACCAGGACCCTCTACA;

AR forward primer
(SEQ ID NO: 3)
5'-CGTTCTTCAAGCCCAAGTGC, reverse primer
(SEQ ID NO: 4)
5'-ATGGGCAGCTTGATGACTGG;

PSA forward primer
(SEQ ID NO: 5)
5'-GTATCACGTCATGGGGCAGT, reverse primer
(SEQ ID NO: 6)
5'-GGTTGATAGGGGTGCTCAGG;

galectin-4 forward primer
(SEQ ID NO: 7)
5'-GATGCCACCTTACCCTGGTC, reverse primer
(SEQ ID NO: 8)
5'-CCTTGCAGCCTCCCGAAATA;

SOX9 forward primer
(SEQ ID NO: 9)
5'-TCTGAACGAGAGCGAGAAGC, reverse primer
(SEQ ID NO: 10)
5'-CCGTTCTTCACCGACTTCCT;

ST3GAL1 forward primer
(SEQ ID NO: 11)
5'-GGCAACCTGAGGGAGTCTTC, reverse primer
(SEQ ID NO: 12)
5'-GTACACCAGATGGTGGGTGG.

1.4 Chromatin Immunoprecipitation

We used web-based software PhysBinder (17) and ChIP Enrichment analysis database (18) to predict MYC binding elements in target genes. 22Rv1-M4 cells were crosslinked with paraformaldehyde, and nuclear extracts were sonicated to shear DNA. ChIP assay was performed using the ChIP kit according to the manufacturer's protocol (Zymo Research, Irvine, CA). The following ChIP Grade antibodies were used for ChIP: MYC (Cat #13987, RRID: AB_2631168, Cell Signaling) and control IgG (Cat #ab172730, Abcam). The solution was then successively washed with low salt, high salt, and LiCl buffer prior to elution. Following RNase and proteinase K digestion and DNA extraction, the immunoprecipitated and control (input) DNA was analyzed by qPCR; negative control primers were designed for the regions approximately 2000 bp upstream of the transcription factor binding site. CHIP qPCR primer: MYC binding site forward primer
(SEQ ID NO: 13)
5'-AGCAGGATCAGAAATGCGGA, reverse primer;
(SEQ ID NO: 14)
5'-CCCTAATGCGAAGGGGTCTG;

negative control forward primer
(SEQ ID NO: 15)
5'-TGGCCAGCCATGACTTATGA, reverse primer
(SEQ ID NO: 16)
5'-AAACTCGTTGGAGTAGGTCGG.

1.5 In Vivo Development of CRPC Model

Male BALB/c nude and NOD-SCID mice (6-8 weeks old) were obtained from the National Laboratory Animal Center (Taiwan), and all animal work was conducted under protocols approved by the Institutional Animal Care and Use Committee, Academia Sinica. For all xenograft studies, after tumors were established, mice were randomly assigned to experimental groups. For the development of castration-resistant cells, suspension of $2\times10^5$ LNCaP cells labeled with luciferase gene (LNCaP-Luc2) in DPBS was orthotopically injected in nude mouse anterior prostate. Following development for 4 weeks, mice were castrated by surgical removal of both testes. The host mice were necropsied, and primary tumors were dissected under laminar flow 7 weeks after castration. Tumor tissues were minced using sterile scalpels and further digested with collagenase D (Roche, Taipei, Taiwan) for 1 h. This procedure was repeated two, three or four times to obtain a primary culture of CRPC, defined as LNCaP-CR2, -CR3 and -CR4, respectively. LNCaP-tetO-Gal4 cells were injected into nude mouse prostates, and after 4 weeks mice were castrated to analyze androgen deprivation response in tumor growth. For the in vivo measurement of bioluminescence imaging (BLI), mice received D-luciferin at 150 mg/kg by intraperitoneal injection, and BLI images were captured with an IVIS Lumina XRMS, thereafter data were processed and quantitatively analyzed using the manufacture's Living Image software (PerkinElmer, Waltham, MA).

1.6 In Vitro Assay for Cell Growth and Colony Formation

For cell growth assay, 5000 LNCaP-tetO-Gal4 cells were seeded in 96-well plates overnight and treated with doxycycline to induce galectin-4 expression for 6 days in CD-FBS medium with or without 1 nM DHT. The medium was refreshed every 2 days. The readouts of cell number were measured by CyQUANT Direct Cell Proliferation Assay (Invitrogen) on a BioTek microplate reader with excitation and emission wavelengths at 510 and 535, respectively. Colony-formation assays in response to treatment were performed by plating $1\times10^3$ LNCaP, LNCaP-CR4 or its derivative cells in a 6-well plate. After 2 days, cells were incubated in CD-FBS medium with or without androgen or treated with drugs for 96 h. After 10 days cells were fixed with 4% paraformaldehyde in PBS and stained with crystal violet solution, and colonies of >50 cells were quantified in FluorChem HD2 system (ProteinSample, San Jose, CA).

1.7 Tumorsphere Assay

For tumorsphere assay, cells were suspended in DMEM/F12 medium (Invitrogen) supplemented with B27 supplement (Invitrogen) and GlutaMAX (Invitrogen). The medium was made semi-solid by the addition of 0.5% Methylcellulose (R&D Systems) to prevent cell aggregation. Cells were seeded in ultra-low attachment 6-well plates (Corning) at a density of 1,000 cells per well. After 10 days, the number of spheres with diameter ≥60 μm was quantified by coulter counter (Beckman Coulter).

1.8 Flow Cytometry

To profile cell surface glycans, cells were detached by Accutase (Innovative Cell Technologies, San Diego, CA) treatment, washed with PBS for three times, and suspended in Carbo-Free Blocking Solution (VECTOR, Burlingame, CA). Cells were incubated with biotin-conjugated lectins, PHA-L (2 μg/mL), PNA (10 μg/mL), MALII (5 μg/mL), Jacalin (5 μg/mL, VECTOR), and galectin-4 (5 μg/mL), or BSA as a control followed by APC-labeled streptavidin. After incubation for 30 min on ice, cells were analyzed on an Accuri C6 flow cytometer (BD Biosciences, Taiwan). Galectin-4 (R&D Systems, Minneapolis, MN) and BSA were biotinylated using Lightning-Link Rapid Conjugation System (Innova Biosciences, Cambridge, UK) following the manufacturer's instructions.

1.9 Immunochemistry Staining

The tumor samples were fixed in 10% neutral-buffered formalin for 20 hours and embedded in paraffin. Tumor sections (4 μm) were deparaffinized and rehydrated in a graded series of ethanol. After antigen retrieval, sections were then incubated with specific primary antibodies, including galectin-4 (Cat #GTX114527, GeneTex) and C1GALT1 (Cat #HPA011294, Sigma-Aldrich) for 1 h. A micro-polymer detection system (Biocare Medical) was used to detect the primary antibodies. All tissue microarray slides were examined and scored by two pathologists. Immunostaining of PCa tissue array was evaluated manually, and the intensity was scored on the following scale: 0: negative, 1: weak, 2: moderate, and 3: strong. The scoring was determined by: distribution of positively stained cells× intensity of the staining. A score of 120 was used as a cutoff value and samples scored high for target expression (score≥120) were compared with all the rest of the samples.

1.10 Statistical Analyses and Public Data Processing

Statistical analysis was performed using GraphPad Prism 7 software. Experimental data are represented as mean±SEM or column scatter plot. P values of less than 0.05 were considered significant using Student's t-test (two-tailed). Survival analyses were performed using the Kaplan-Meier method, and the significance, hazard ratio (HR) and 95% CI were compared by the Log-rank test. Correlation between groups was determined by computing Pearson correlation coefficient r and the associated P value. The microarray data in this paper have been submitted to the Gene Expression Omnibus (GEO) database with the accession numbers GSE100301. Gene expression datasets from multiple, previously reported human PC specimen cohorts, GSE32269, GSE21032, GSE70770, and GSE35988, were downloaded from GEO. Gene Set Enrichment Analysis (GSEA) was carried out using the GSEA software package (19) to assess the enriched signatures in an unbiased fashion against the Molecular Signatures Database (MSigDB) with filtering criteria of a P value of less than 0.05 and FDR q<0.25. Z ratios are calculated by taking the difference between the averages of the observed gene Z scores and dividing by the SD of the z-differences distribution. The MYC activity score for each PCa sample in the published datasets was computed by summing the z-score values of MYC target genes that were previously validated by ChIP-qPCR in LNCaP cells (20).

Figure 1A:
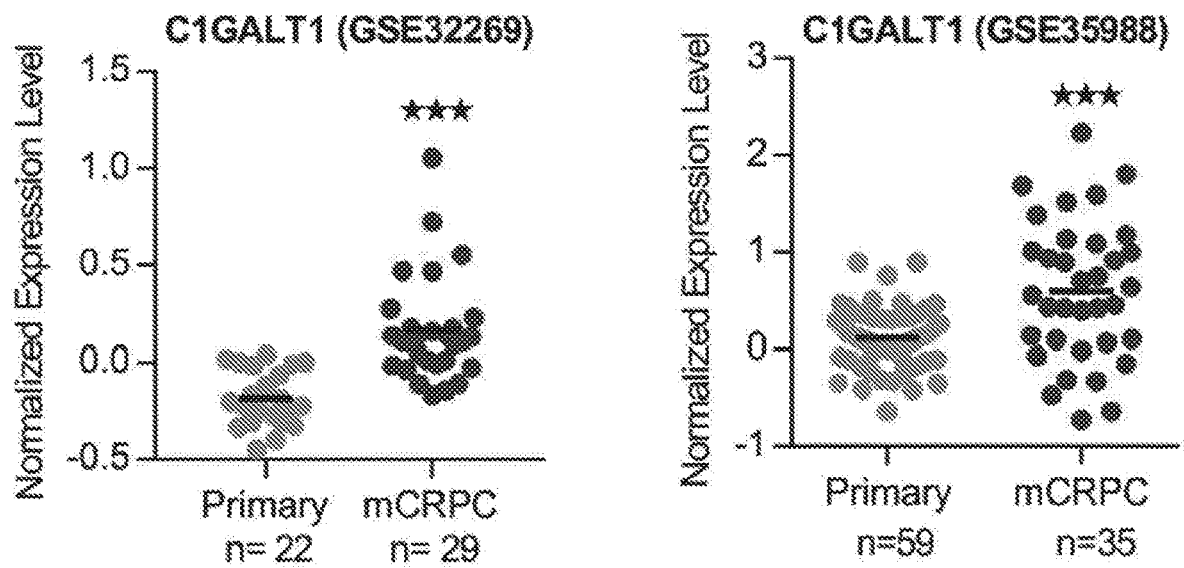
FIG. 1A to FIG. 1B represent glycosylation gene expression in mCRPC.
Figure 1B:
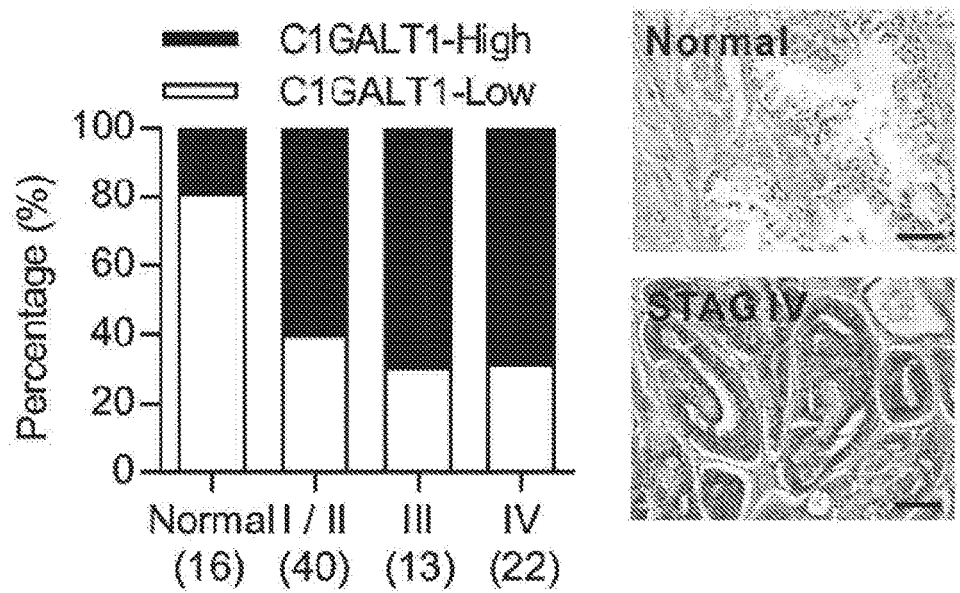

2. Results 2.1 Systematic Analysis of Glycogene Expression Reveals a Correlation Between C1GALT1-Mediated O-Glycans and Metastasis and Poor Survival in Clinical PCa To investigate the changes in glycosylation in PCa progression, we explored the expression level of the glycosyltransferases (glycogenes) in four transcriptomic datasets of PCa from patients using the KEGG PATHWAY database of N-glycan biosynthesis, mucin-type O-glycan biosynthesis, O-mannose glycans biosynthesis, glycosaminoglycan biosynthesis, and glycosphingolipid biosynthesis (21-23). The glycan biosynthesis signatures in four PCa cohorts (GSE21032, GSE35988, GSE70770, and GSE32269) were analyzed by computing the sum Z score of each individual genes in glycan biosynthesis gene sets of KEGG. Heat map presents the differential expression of signatures (Z ratio), and the differential expression of glycogenes (Z ratio) in primary and metastatic (or mCRPC) tumor samples are presented as a heat map (data not shown). By computing the sum of Z score of genes in each gene set, we found the increased activity of mucin-type O-glycan biosynthesis pathway stands out in metastasis tumors or mCRPC compared to primary tumors. The analysis further revealed that expression of T antigen synthase C1GALT1 of core 1 O-glycosylation and the capping (sialylation) enzyme ST3GAL1 in mCRPC was higher than in primary PCa, whereas core 2 O-glycan branching genes (GCNTs) exhibited a tendency to downregulation and N-glycosylation glycogenes showed no significant variation (FIG. 1A). IHC analyses of another PCa tissue microarray further revealed that C1GALT1 was expressed at high levels in 70% of PCa tumor samples and correlated with advanced tumor stages (FIG. 1B).

Figure 2A:
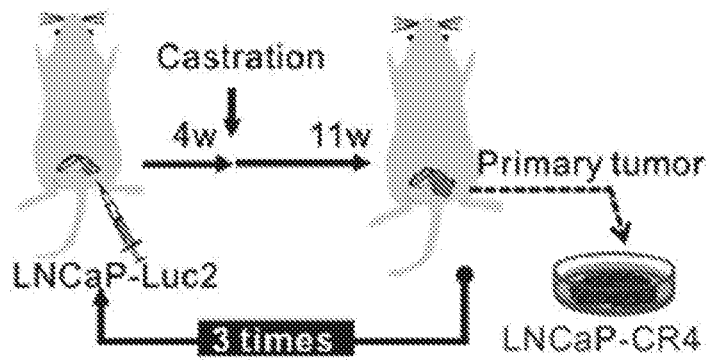
FIG. 2A to FIG. 2I show that C1GALT1 is required for maintaining castration resistance during CRPC progression and in the LNCaP tumor model.
Figure 2A:
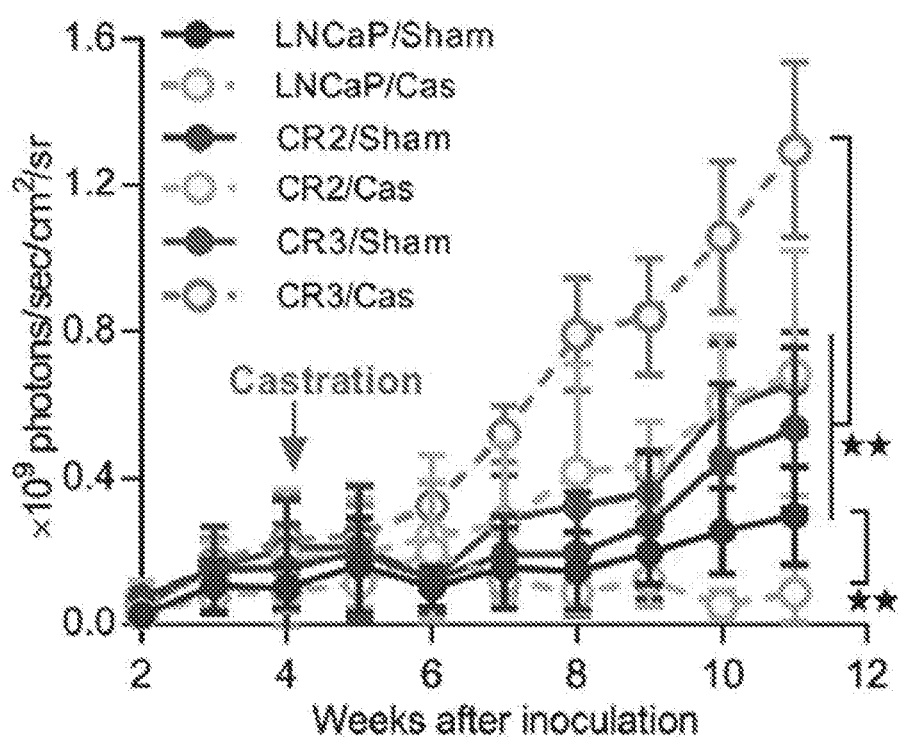
Figure 2B:
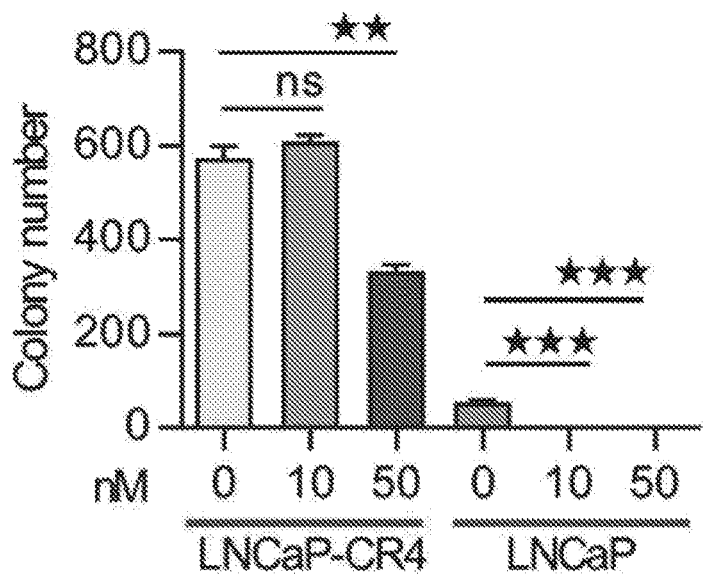
Figure 2C:
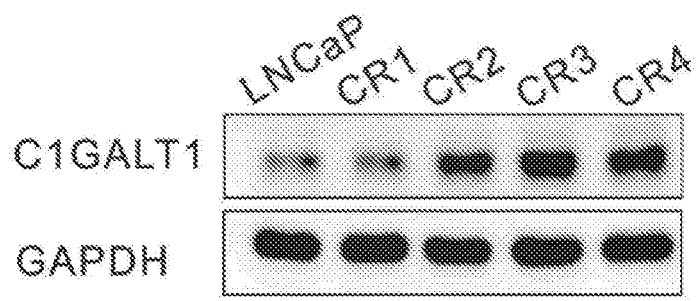
Figure 2D:
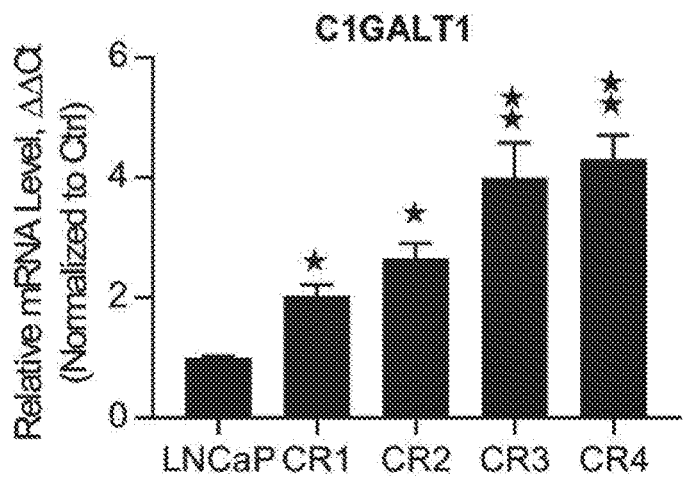
Figure 2E:
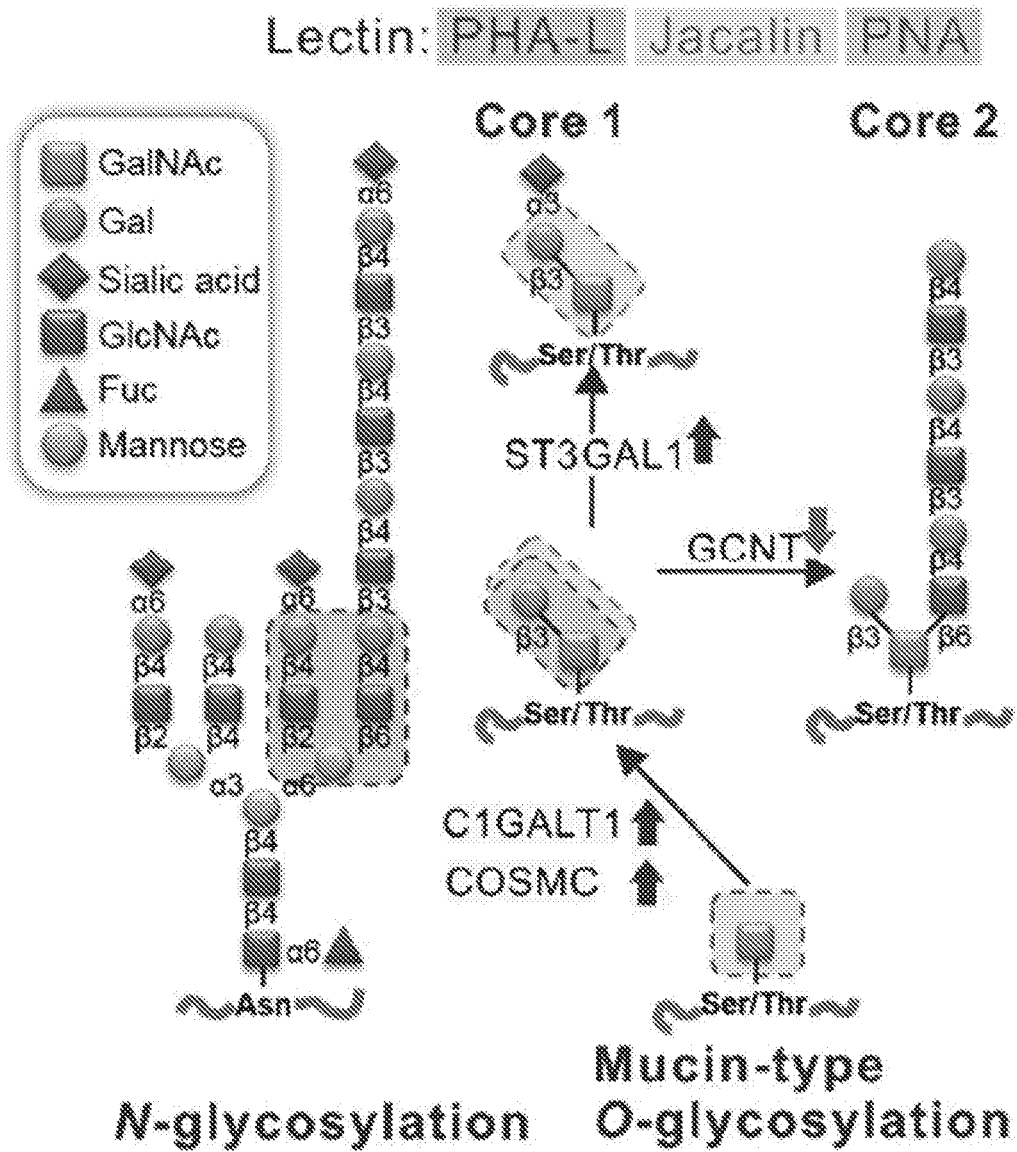
Figure 2F:
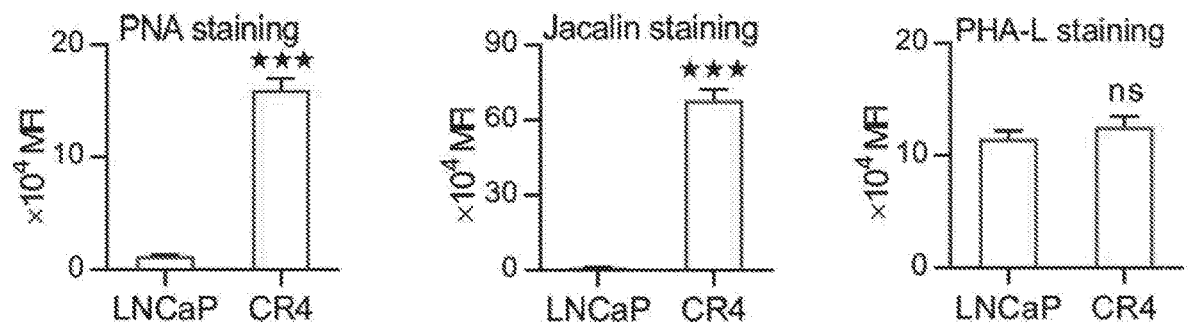
Figure 2G:
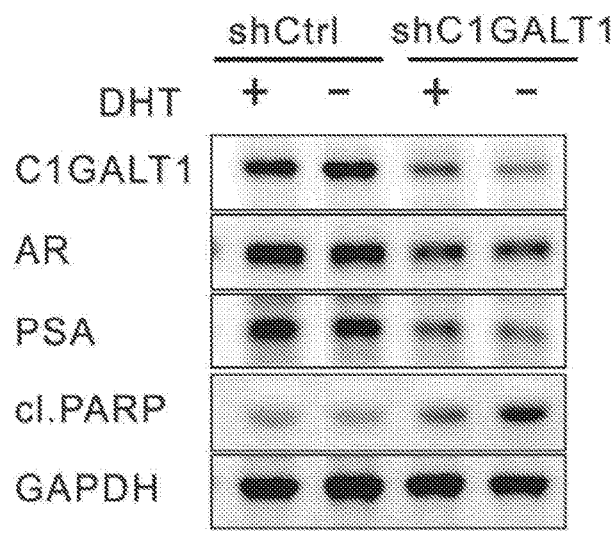
Figure 2H:
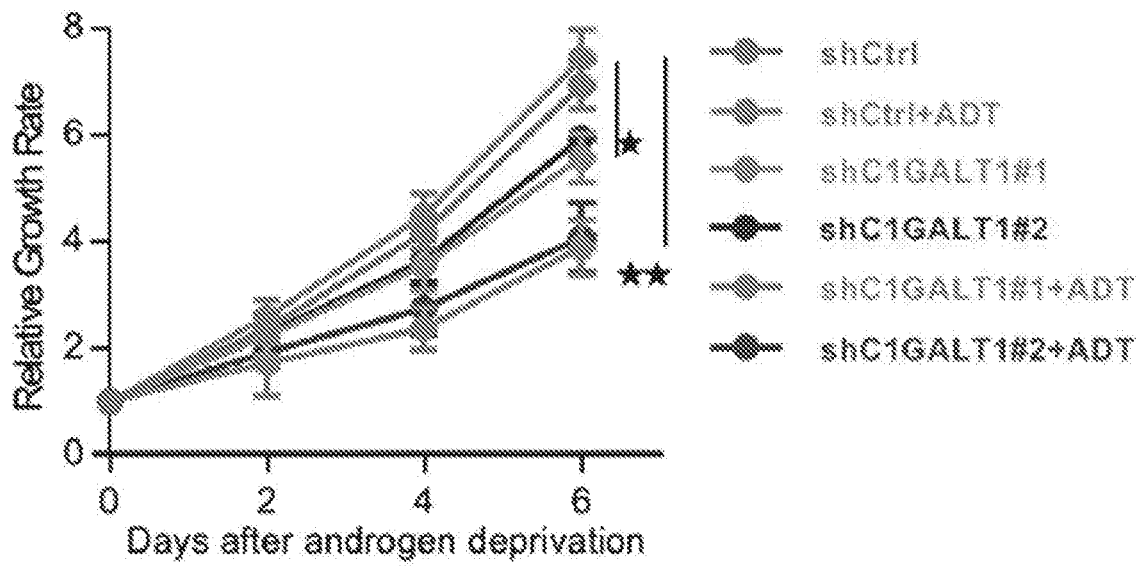
Figure 2I:
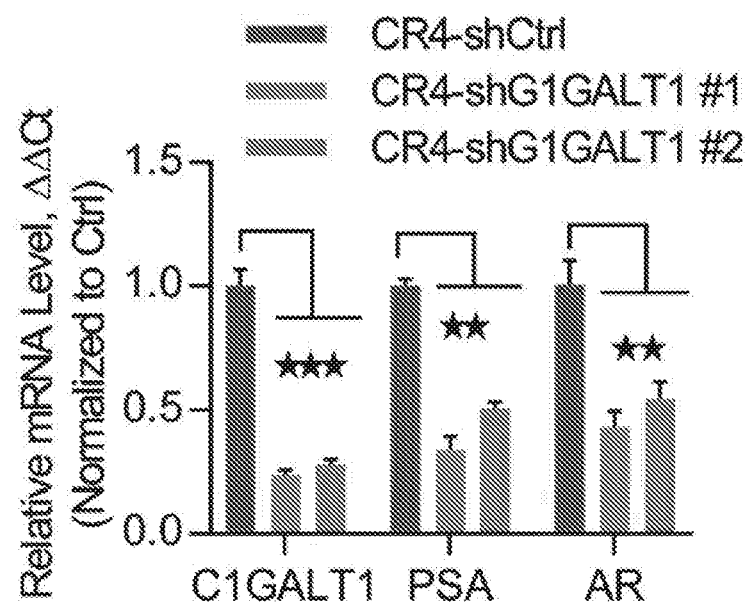

2.2 C1GALT1 Expression is Upregulated During PCa Progression in Xenograft Models and Promotes Castration Resistance Since C1GALT1 expression was associated with CRPC and is essential for O-glycan biosynthesis, we examined whether C1GALT1 plays any role in CRPC progression. First, we recreated the in vivo progression of CRPC by growing castration-sensitive LNCaP xenografts in nude mouse prostate and deprived the mice of androgen by castration (FIG. 2A). This procedure was repeated three times to obtain a series of primary cultures of CRPC, defined as LNCaP-CR2, -CR3, and -CR4, respectively. Compared to parental LNCaP tumors, LNCaP-CR2 and CR3 tumors continued to grow after castration as determined by BLI (bioluminescence imaging) curve and end-point tumor mass, representing the castration-resistant phenotype (FIG. 2A). LNCaP-CR4 cells also exhibited resistance to enzalutamide in clonogenic growth (FIG. 2B). Importantly, the CRPC cell lines expressed elevated mRNA and protein levels of C1GALT1 (FIG. 2C, D). Moreover, the LNCaP-derived CRPC cell lines displayed increased expression of T and sialyl-T antigens stained by PNA and jacalin lectins, but invariable levels of N-glycan as indicated by PHA-L staining (FIG. 2E, F). Downregulation of C1GALT1 sensitized LNCaP-CR4 cells to ADT, as indicated by increased apoptosis (PARP cleavage) and decreased growth in LNCaP-CR4 cells growing in CD-FBS medium compared to in androgen (1 nM DHT)-containing medium (FIG. 2G, H). Furthermore, the suppression of C1GALT1 also lowered the expression levels of AR and downstream PSA (FIG. 2I).

Figure 3A:
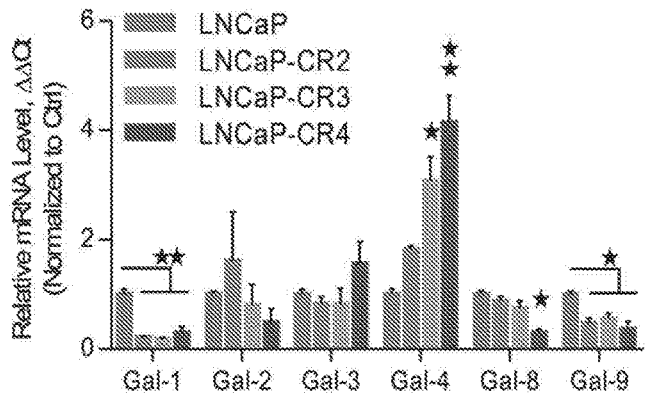
FIG. 3A to FIG. 3G show that galectin-4/O-glycan signaling mediates RTK activation and castration resistance.
Figure 3B:
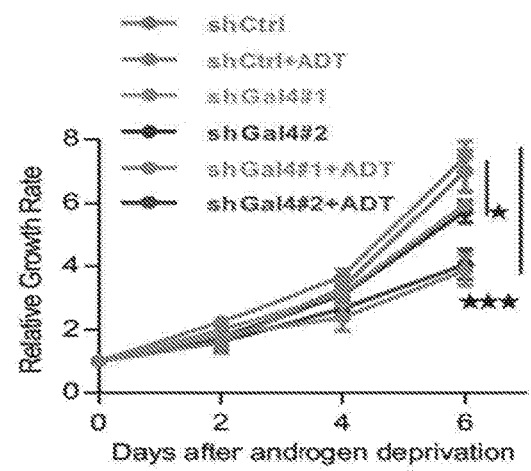
Figure 3C:
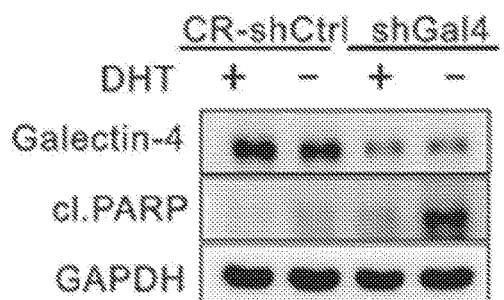
Figure 3D:
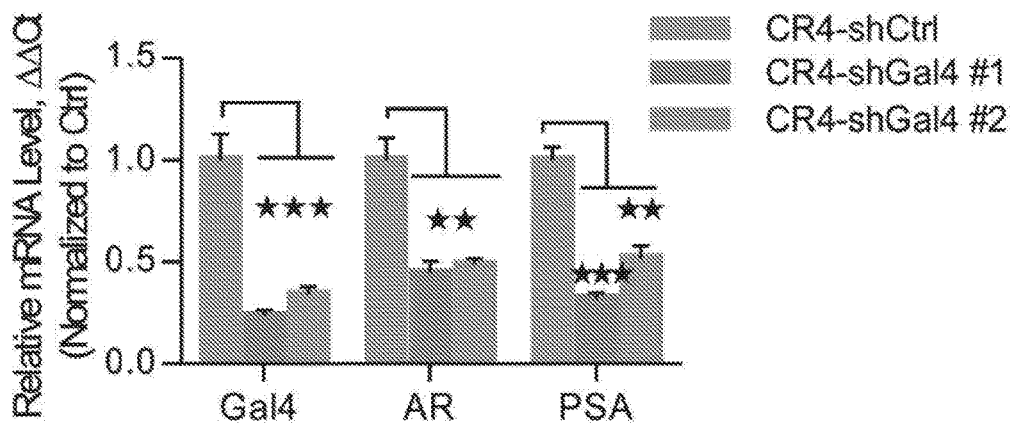
Figure 3E:
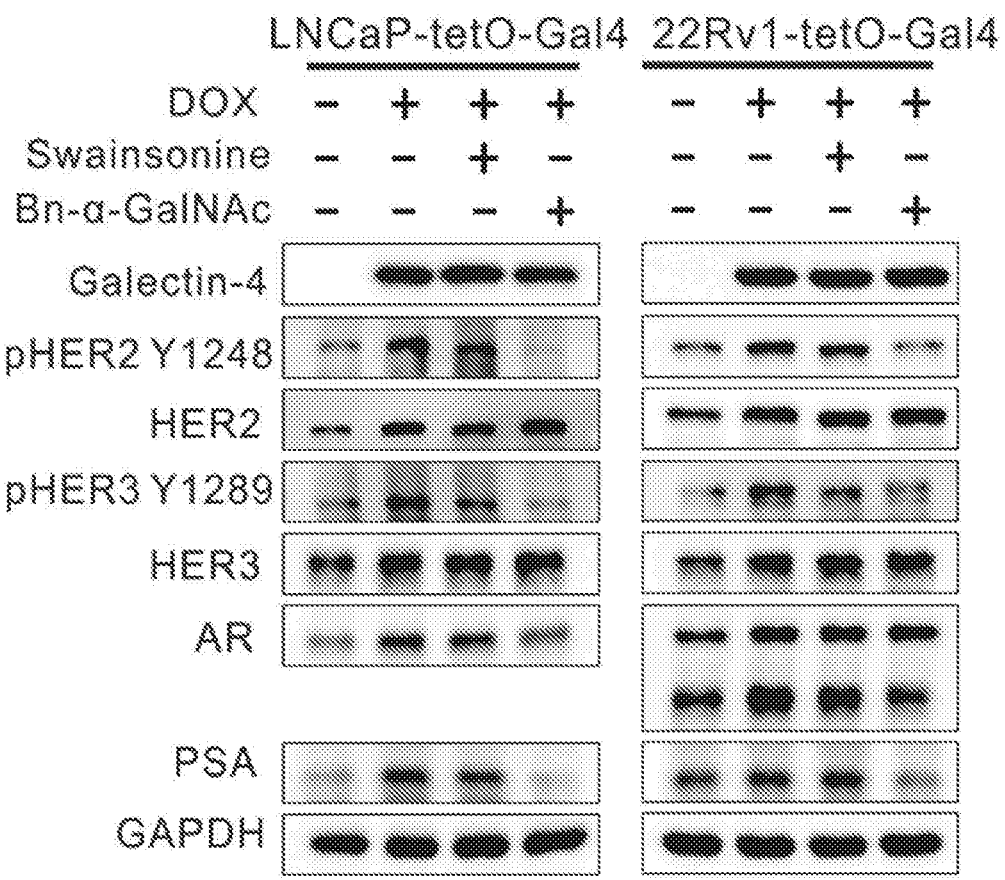
Figure 3F:
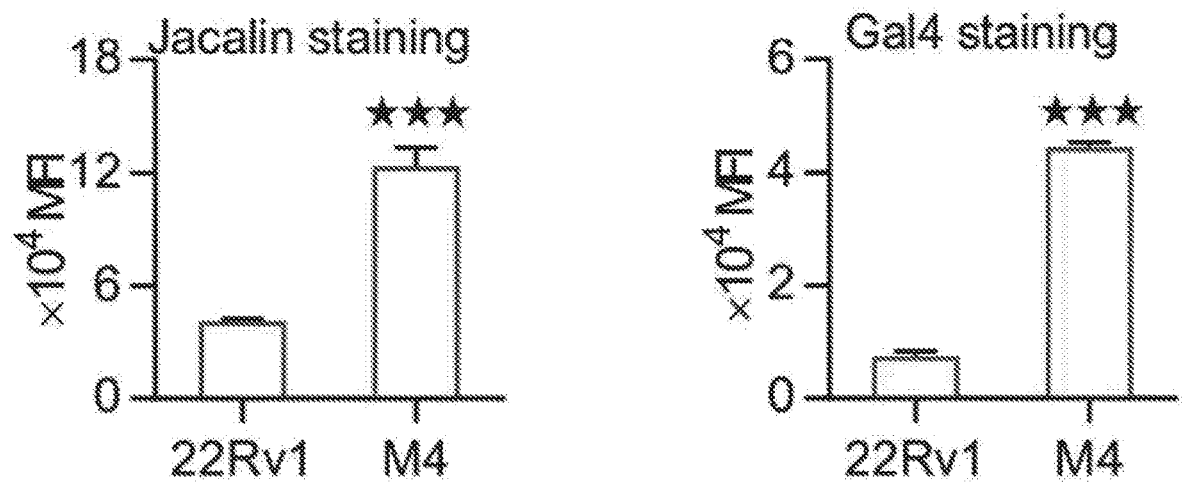
Figure 3G:
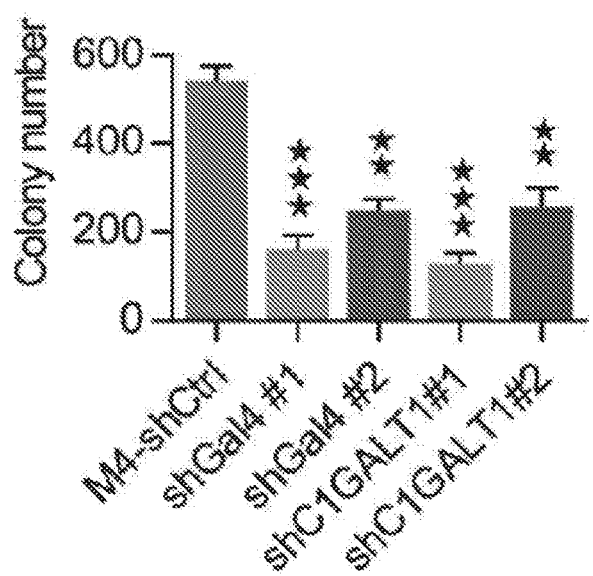
Figure 8A:
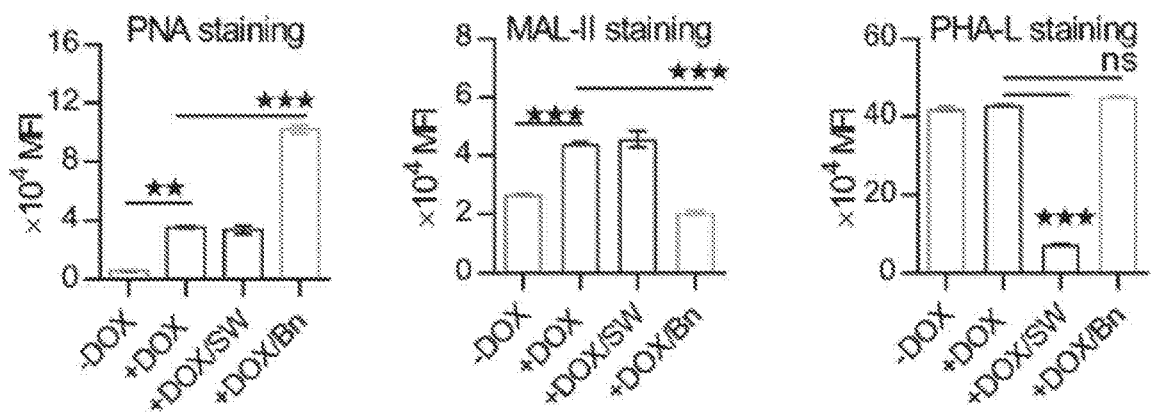
FIG. 8A to FIG. 8C show the characterization of glycophenotype in prostate cancer cells.
Figure 8B:
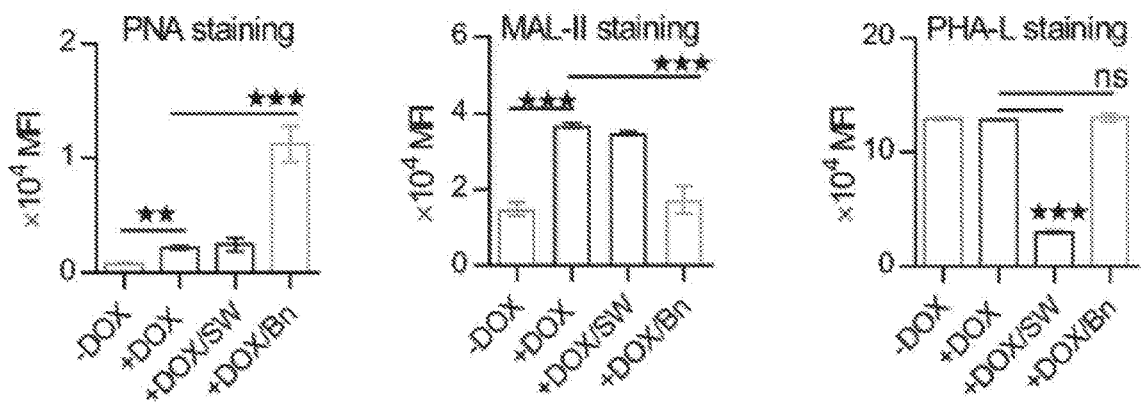
Figure 8C:
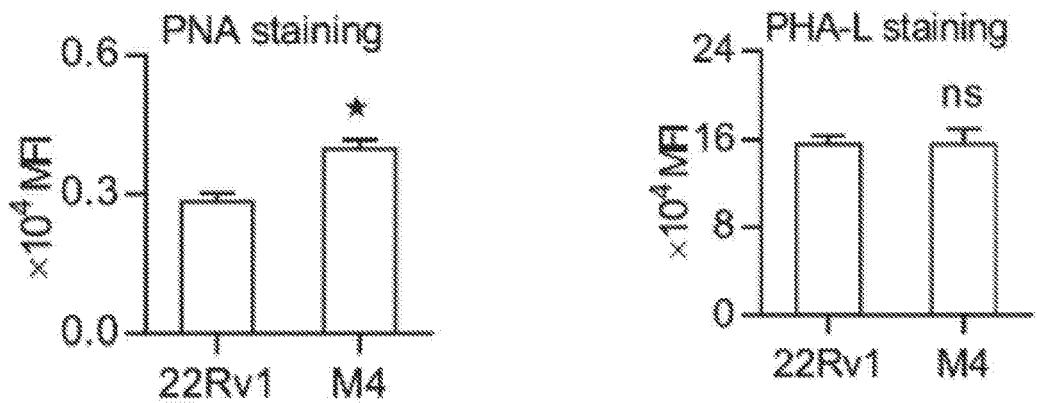

2.3 Galectin-4 Engaged with C1GALT1-Meditated Glycan Promotes AR Signaling, Castration Resistance, and Colony Growth by Activating RTKs Increasing evidence suggests that aberrant glycosylation, such as T and sialyl-T antigens on the cancer cell surface may be involved in promoting cancer progression by interaction with galectins, which themselves are frequently overexpressed in the tumor microenvironment (15, 24, 25). To examine the potential role of galectins in PCa progression, we explored the expression levels of galectins in public transcriptomic datasets. The datasets showed that galectin-4 expression in mCRPC patients was consistently higher than in primary PCa ((data not shown)). Consistently, LNCaP-CR4 series of cells exhibited progressively increasing galectin-4 expression compared with parental cells (FIG. 3A). Depleting galectin-4 by shRNA sensitized LNCaP-CR4 cells to ADT in growth assay and apoptosis (PARP cleavage), also lowered the expression levels of PSA and AR in LNCaP-CR4 cells (FIG. 3B-D). Recent data showed that galectin-4 expression activates EGFR, HER2, HER3, and IGF1R in a glycan-dependent manner (26). Also, the activation of HER2/3 and IGF1R are associated with clinical CRPC and reported to support CRPC in xenograft models (2, 27). To determine whether galectin/glycan signaling regulates HER2/3 phosphorylation and AR signaling, the galectin-4 expressing LNCaP and 22Rv1 PCa cells were treated either with benzyl-α-GalNAc, a pseudosubstrate to inhibit O-glycosylation, or swainsonine, an α-mannosidase II inhibitor to stop N-glycosylation maturation. While swainsonine treatment indeed decreased the PHA-L staining for N-glycans, it did not affect the HER2/3 phosphorylation and the induction of AR and PSA protein expression (FIG. 3E and FIG. 8A, 8B). On the other hand, benzyl-α-GalNAc blocked the galectin-4-mediated activation of HER2/3 and AR signaling. In PCa cells, benzyl-α-GalNAc interfered mucin-type O-glycosylation by decreasing the α2,3-sialylation of core 1 O-glycans, therefore reduced the binding of treated cells to MALII and increased binding to PNA. These data also suggest that α2,3-sialylated core 1 O-glycans essentially mediate the RTKs activation by galectin-4 thus the resulting CRPC progression (FIG. 3E and FIG. 8A, 8B). In line with this finding, upregulated galectin-4 and C1GALT1 expression were also observed during the progression of CRPC cell line 22Rv1 into metastatic 22Rv1-M4 cells, derived from in vivo lymph node metastases and exhibited high levels of metastatic ability (26). The flow cytograms of lectin staining showed a right shift in the PNA and jacalin curves, indicating a difference in cell-surface O-glycosylation in 22Rv1-M4 cells compared with their parental cells, while N-glycans stained by PHA-L lectin remained unaltered (FIG. 3F and FIG. 8C). The glycophentyping data also suggested an increase in core 1 O-glycans with a concomitant increase in galectin-4 binding sites in PCa cells expressing a high level of C1GALT1 (FIG. 3F). Downregulation of either galectin-4 or C1GALT1 in 22Rv1-M4 significantly suppressed colony formation ability (FIG. 3G).

Figure 4A:
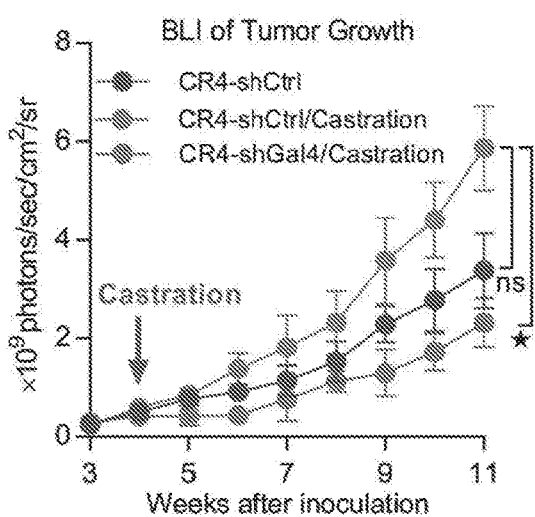
FIG. 4A to FIG. 4F show that galectin-4 expression promotes castration resistance and metastasis in an orthotopic prostate cancer xenograft model.
Figure 4B:
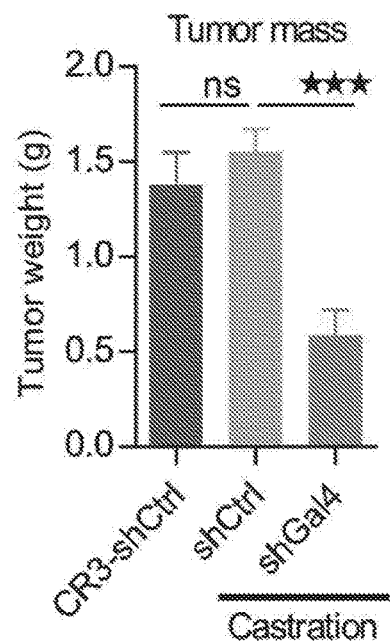
Figure 4C:
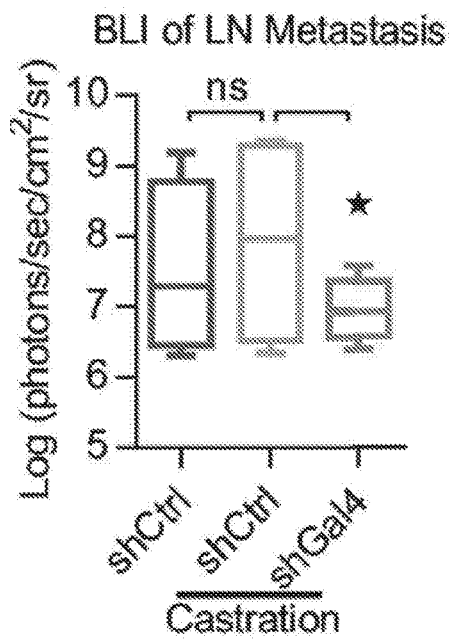
Figure 4D:
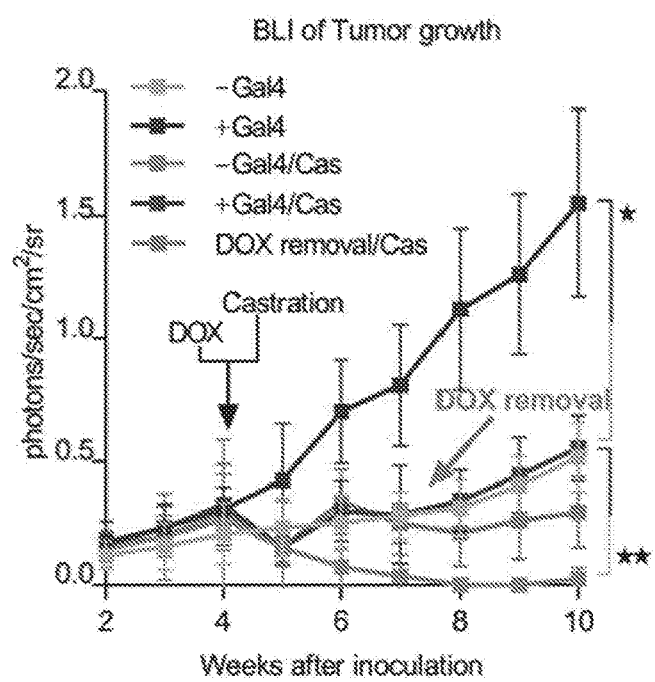
Figure 4E:
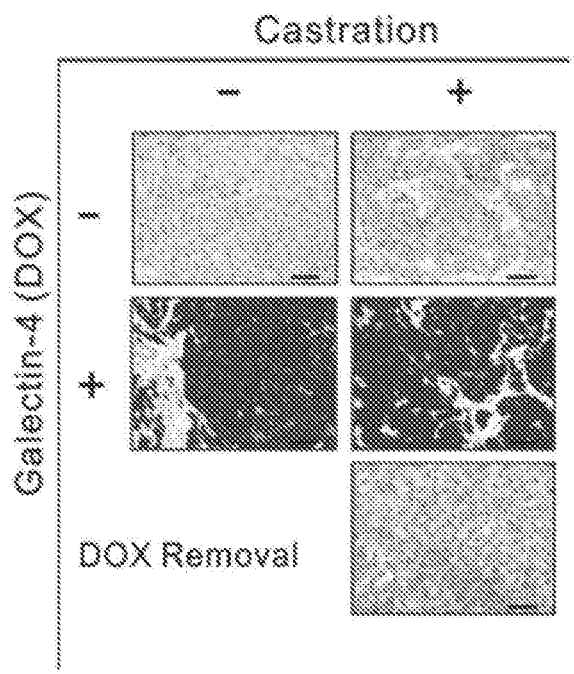
Figure 4F:
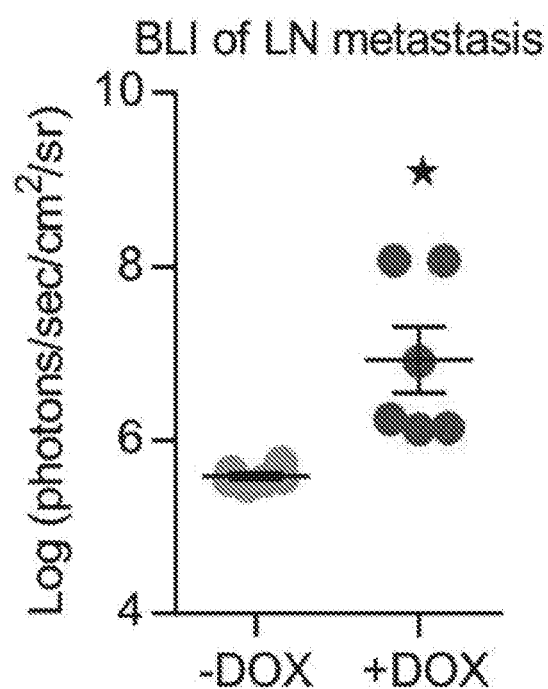

2.4 Galectin-4/O-Glycan Signaling Promotes not Only Castration-Resistant Growth but Also Metastasis In Vivo In vivo, downregulation of galectin-4 sensitized the LNCaP-CR4 tumors to castration treatment compared to LNCaP-CR4 control tumors by inhibiting primary tumor growth and lymph node metastasis, suggesting the castration-resistant growth of LNCaP-CR4 had galectin-4 signaling activity (FIG. 4A-C). To determine whether exogenous galectin-4 expression can recapitulate the aggressive phenotype in PCa, we forced galectin-4 overexpression in androgen-dependent LNCaP cells using the tetracycline-inducible system. We found that galectin-4 overexpression enhanced the LNCaP tumor growth in nude mice compared to control treatment and completely abolished the castration-induced tumor regression (FIG. 4D, E). Deprivation of galectin-4 by withdrawing doxycycline in established tumor slowed the tumor growth compared with persistent galectin-4 expressing tumors (FIG. 4D, E). Furthermore, galectin-4 also promoted lymph node metastasis in an LNCaP orthotopic tumor model, as analyzed by ex vivo BLI and IHC (FIG. 4F).

Figure 9A:
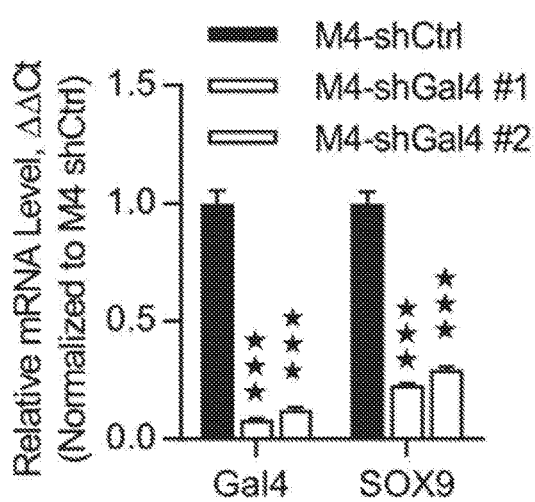
FIG. 9A to FIG. 9F show that galectin-4 expression mediates cancer stem cells properties in PCa cells.
Figure 9B:
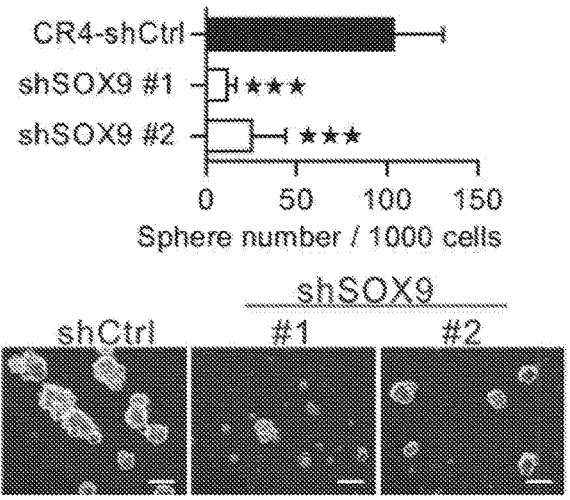
Figure 9C:
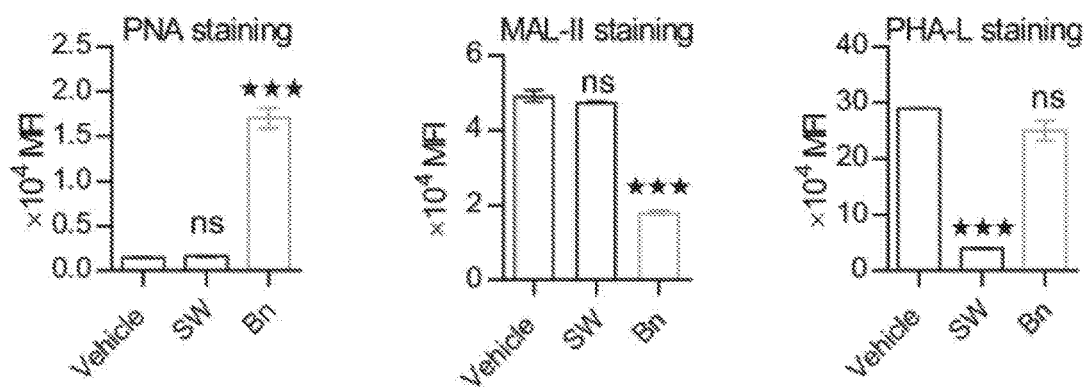
Figure 9D:
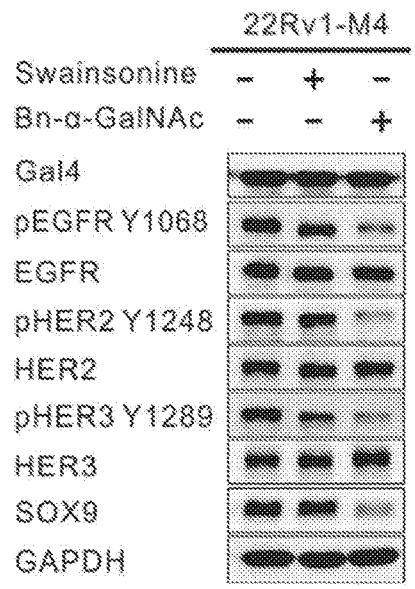
Figure 9E:
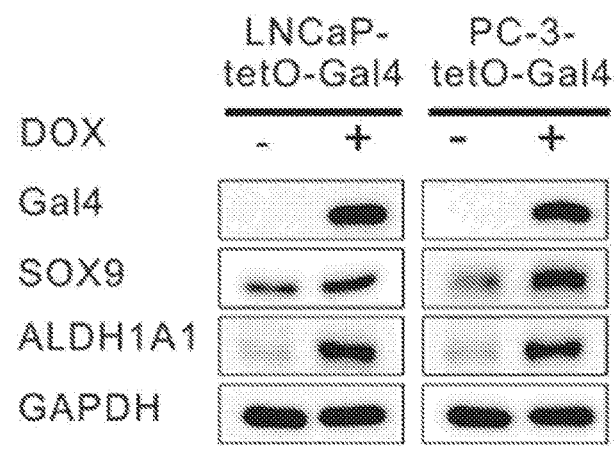
Figure 9F:
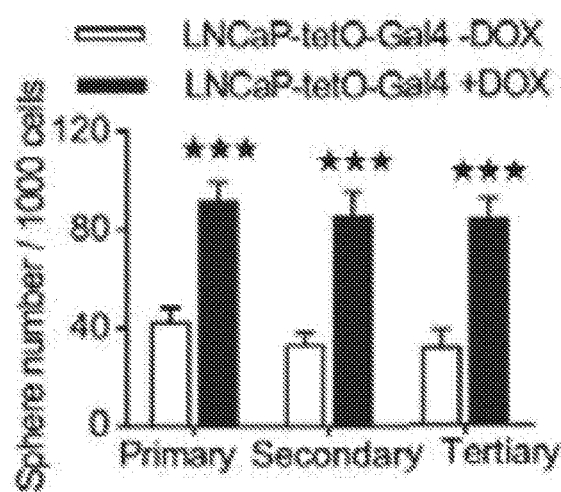
Figure 9F:
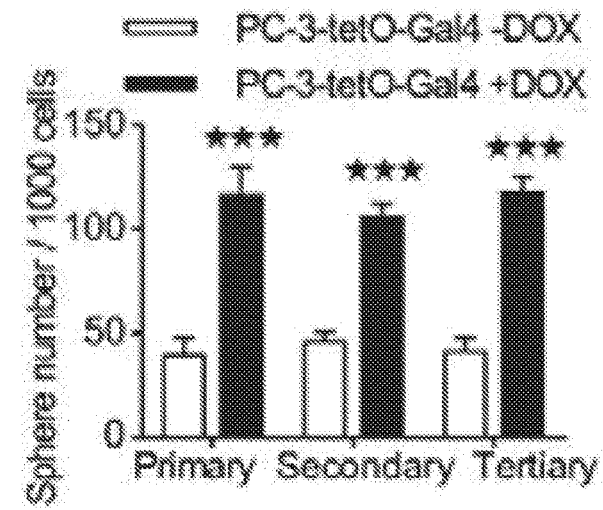

2.5 Galectin-4/O-Glycan Signaling Promotes SOX9 Expression, Cancer Cell Stemness Properties, and Metastasis Via Activation of RTKs To understand the mechanisms of galectin/glycan signaling for metastasis, we analyzed the genome-wide responsive genes using cDNA microarray by comparing ectopic expression of galectin-4 and control vector in parental cells, LNCaP and 22Rv1, or control and galectin-4 knockdown conditions in 22Rv1-M4 expressing a high level of galectin-4. Analysis of galectin-4 responsive genes using Gene Set Enrichment Analysis (GSEA) and curated gene sets from the Molecular Signature Database (MSigDB) showed that HER2 signaling, O-glycan biosynthesis, and cancer stem cell signature were enriched in PCa cells depending on galectin-4 expression (FIG. 5A). Given that high expression of galectin-4 in PCa patients was associated with metastasis, next, we investigated the function of galectin-4-mediated signaling in cancer stem cells. Genome-wide analysis showed that galectin-4 expression upregulated SOX9 (data not shown), a transcriptional factor involved in stem cell regulation (28). In vitro, galectin-4 knockdown in 22Rv1-M4 cells significantly decreased SOX9 expression and the sphere-forming aptitude, a reputable CSC characteristic (FIG. 5B and FIG. 9A). Consistently, SOX9 deprivation reduced the tumorsphere in 22Rv1-M4 and LNCaP-CR4 cells (FIG. 5C and FIG. 9B). In experimental metastasis, depletion of SOX9 significantly inhibited the metastatic colonization of 22Rv1-M4 cells, indicating the essential role of galectin-4 and SOX9 in regulating metastatic colonization (FIG. 5D). Having demonstrated the necessary role of SOX9 in regulating metastatic colonization, we further studied the pathway through which galectin-4 regulates SOX9 expression. Treatment of 22Rv1-M4 cells with O-glycosylation inhibitor significantly inhibited SOX9 expression while N-glycosylation inhibitor did not affect SOX9 expression (FIG. 9C, 9D). Also, C1GALT1 knockdown in 22Rv1-M4 cells inhibited SOX9 and ALDH1A1 expression and decreased tumorsphere formation (FIG. 5E, 5F). Conversely, ectopic expression of galectin-4 in LNCaP and PC-3 PCa cells increased the expression of CSC markers, SOX9 and ALDH1A1 and boosted their growth into tumorspheres in serial propagation, suggesting galectin-4 drives clonogenic growth and cell survival signaling regardless of growth factor deficiency (FIG. 9E, 9F). Altogether, the interaction of galectin-4 and C1GALT1-dependent O-glycans activated the signaling for CSC properties and promoted in vivo metastatic colonization.

Figure 6A:
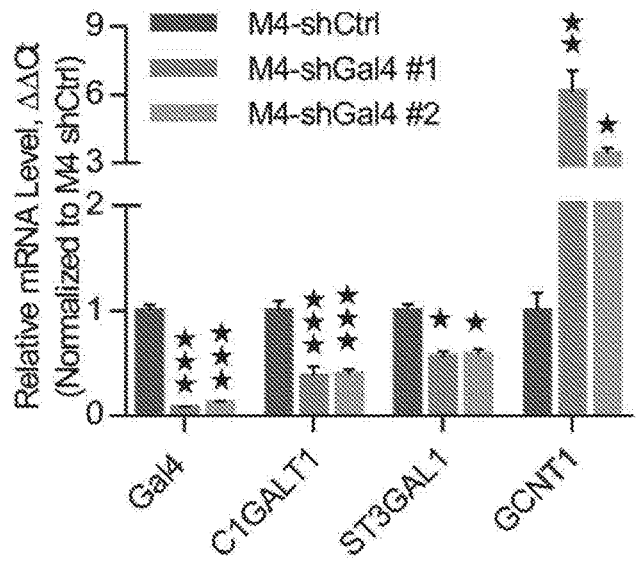
Figure 6B:
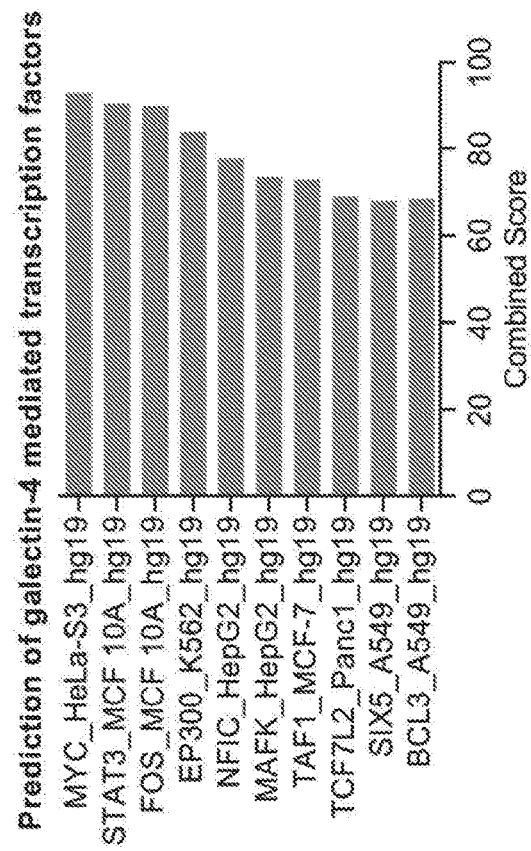
Figure 6C:
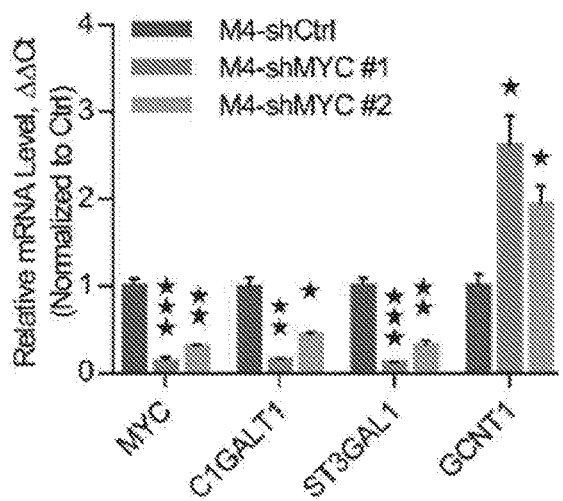
Figure 6D:
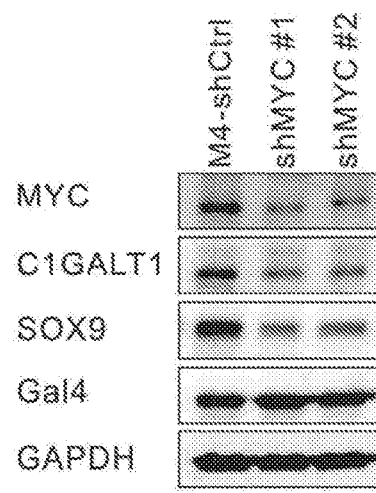
Figure 6E:
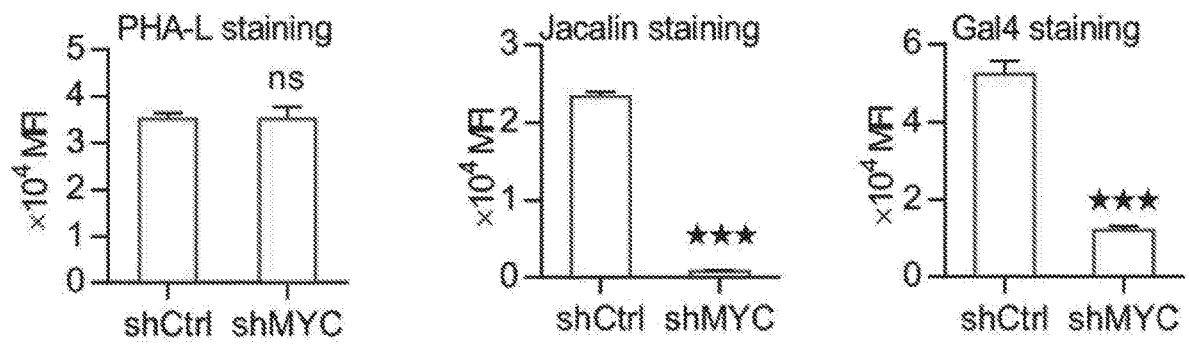
Figure 6F:
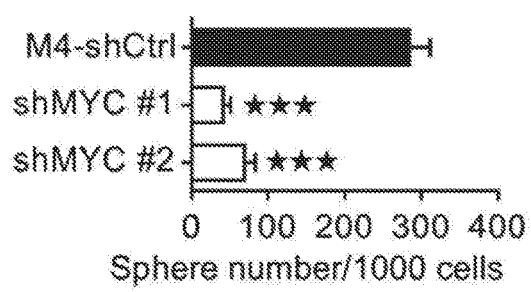
Figure 6F:
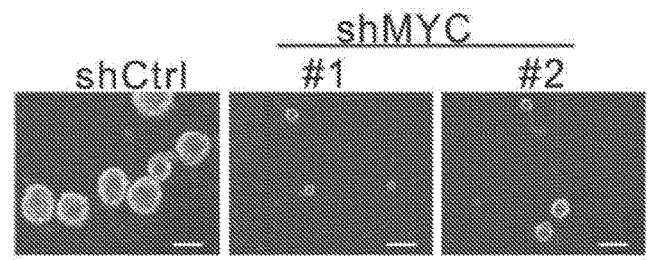
Figure 6J:
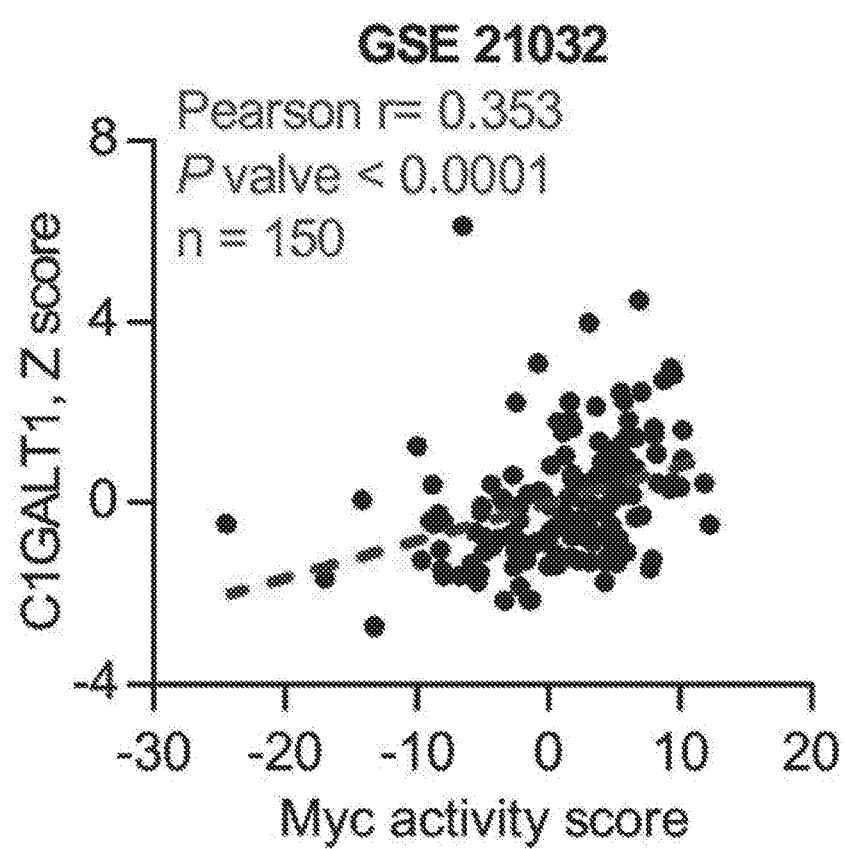

2.6 Galectin-4 Feed-Forward Upregulates its Binding Sites and Downstream Signaling by Altering the Specific O-Glycosylation Pathway Since galectin-4/SOX9 signaling is dependent on C1GALT1-mediated O-glycosylation and the concomitant overexpression along with PCa progression; we next investigated whether expression of galectin-4, C1GALT1 and protein O-glycosylation may be mutually regulated. Downregulation of galectin-4 in 22Rv1-M4 cells significantly decreased the gene expression of C1GALT1 and ST3GAL1 in core 1 O-glycosylation whereas the core 2 branching enzyme GCNT1 was upregulated, suggesting galectin-4 expression upregulated the gene expression of specific O-glycosylation enzymes to modulate the protein O-glycosylation (FIG. 6A). To identify the galectin-4 downstream regulator that alters the protein glycosylation, we performed enrichment analysis of galectin-4-mediated differential genes using an Enrichr algorithm and the ENCODE TF ChIP-seq database (18). Among the enriched transcription factors, we found C1GALT1 listed in the MYC target genes (FIG. 6B). Knockdown of MYC decreased the expression level of C1GALT1 and ST3GAL1 and increased GCNT1 without varying galectin-4 expression (FIG. 6C, D). Also, the MYC knockdown decreased sialylated core 1 O-glycans stained by jacalin, not N-glycans stained by PHA-L in 22Rv1-M4 cells, resulting in loss of the galectin-4 binding sites, downstream SOX9 expression, and tumorsphere formation activity compared to the control knockdown (FIG. 6D-F). On the other hand, MYC overexpression upregulated C1GALT1 and ST3GAL1 expression in LNCaP cells but did not promote the galectin-4 and SOX9 expression, suggesting expression of both galectin-4 and altered O-glycan are required to regulate the CSCs properties (FIG. 10A, 10B). Indeed, MYC activation by overexpression in PCa cells led to more binding sites for exogenous galectin-4 at the cell surface, therefore a right shift of the galectin-4 staining curve was observed in flow cytometry assays (FIG. 6G). Furthermore, immunoprecipitation of HER2 followed by lectin blotting revealed the direct binding of galectin-4 and jacalin to HER2 molecules, which was abolished by the knockdown of MYC (FIG. 6H). Gene regulation of C1GALT1 by MYC was analyzed by chromatin immunoprecipitation (ChIP-PCR) assay. The MYC antibody-specific enrichment of C1GALT1 promoter demonstrated a direct binding of MYC to the promoter sequence of C1GALT1 in 22Rv1-M4 (FIG. 6I). Upon RTK action, ERK phosphorylated MYC at Ser62, thus stabilizing MYC protein and its transcriptional activity (29). Immunoblotting showed that MEK1/2 inhibitor blocked the induction of MYC and C1GALT1 compared to vehicle treatment in 22Rv1-M4 and galectin-4-expressing 22Rv1 and LNCaP cells (FIG. 10C). In agreement with the data above, C1GALT1 expression in clinical PCa specimens significantly correlated with MYC activity in a public PCa transcriptome dataset (FIG. 6J). Together, these data suggest that MYC regulates the abnormal O-glycosylation in cell-surface RTKs and thus primes the cells for binding to galectin-4 and downstream signaling pathways that enable tumor regeneration and metastasis.

Figure 7D:
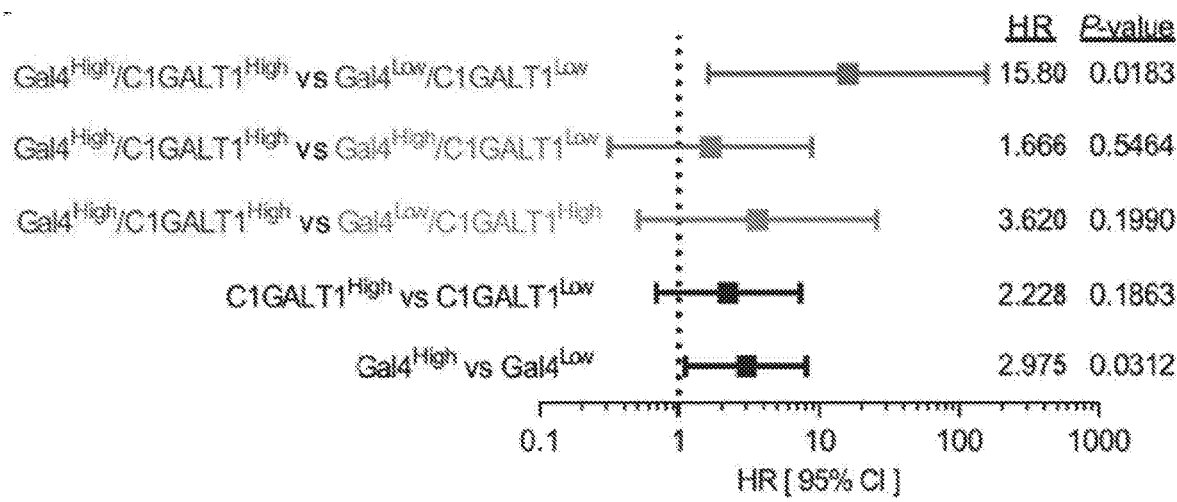
Figure 7E:
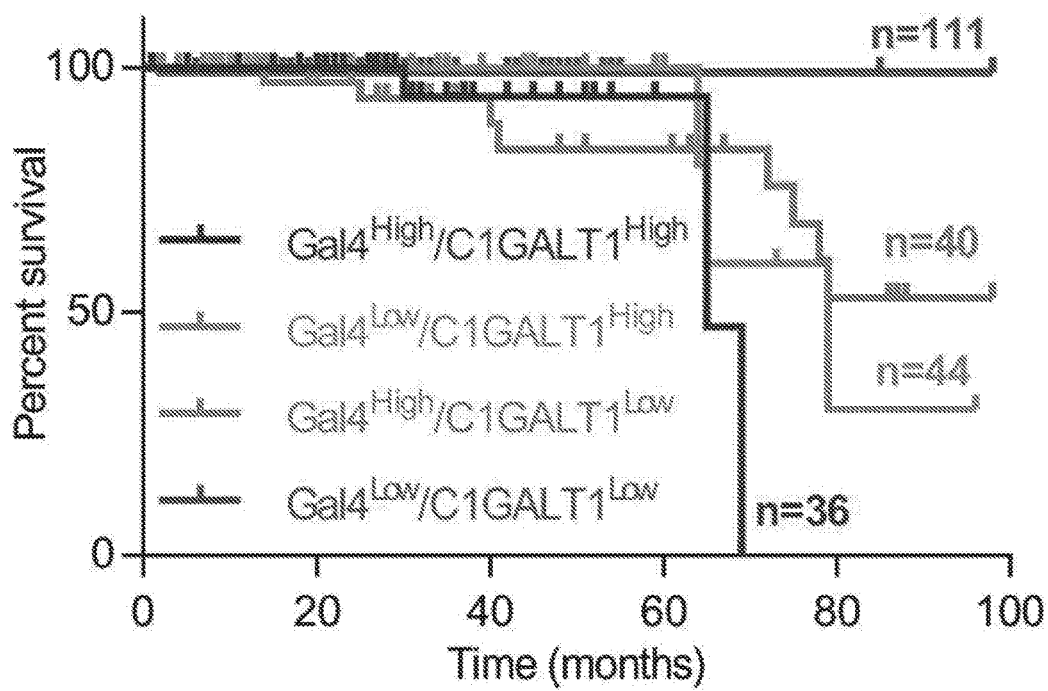
Figure 7F:
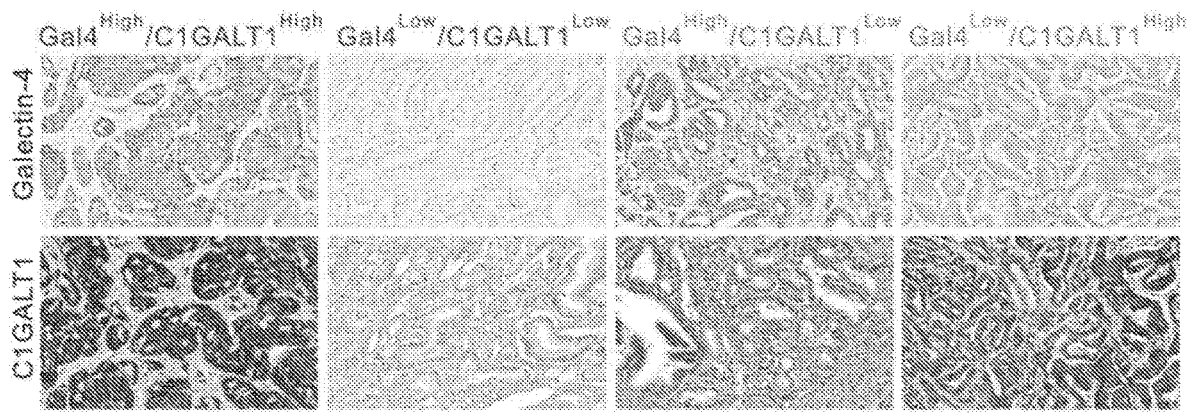
Figure 7G:
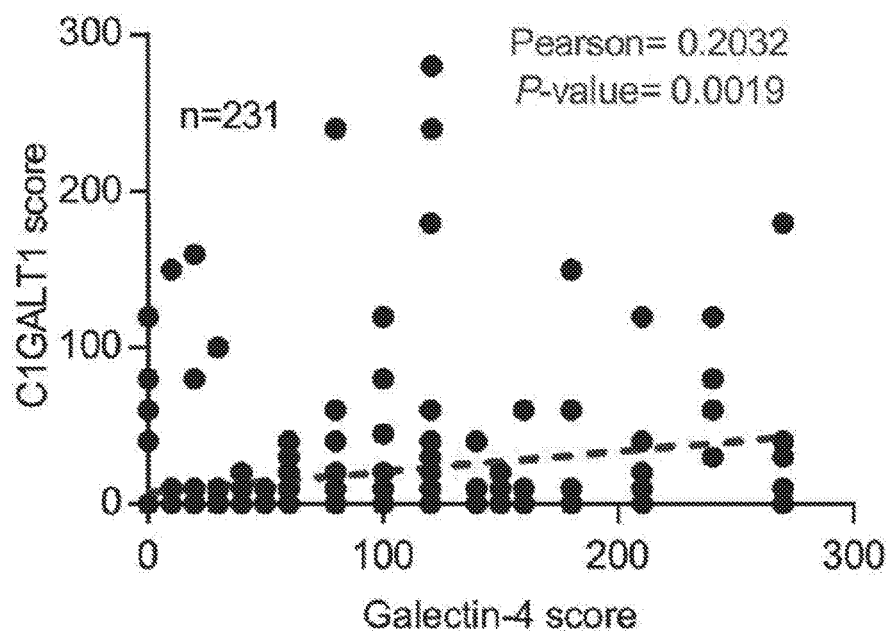

2.7 C1GALT1 and Galectin-4 Expression Exhibit a Synergistic Interaction Resulting in Poor Overall Survival Regarding the critical role of C1GALT1 in mediating galectin-4 signaling in CRPC progression, we next examined the clinical correlation of C1GALT1 and galectin-4 in PCa specimens. The mRNA levels of galectin-4 and C1GALT1 in primary PCa were higher than their paired adjacent normal tissues, as determined by qRT-PCR (FIG. 7A). We found a positive correlation between the tumor expression of galectin-4 and C1GALT1 in this cohort (FIG. 7B). Moreover, Pearson correlation analysis highlighted the strong correlation between the expression of C1GALT1 and galectin-4 in another PCa cohort, suggesting their involvement in an interconnected signaling networks and upregulation during PCa progression in majority of patients (FIG. 7C). To further investigate the prognostic potential of C1GALT1 and galectin-4 in PCa patients, we analyzed the hazard ratio (HR) for overall survival according to the tumor expression of C1GALT1 and galectin-4 in PCa patients treated at the Tri-Service General Hospital in Taipei (n=231) by Cox proportional hazard model. Patients with PCa expressing high galectin-4 had a higher HR (2.975) than those with low galectin-4 (the low galectin-4 expression means an average of galectin-4 mRNA expression level in the tumor not significantly higher than the paired adjacent normal tissue of the same PCa patient) (FIG. 7D). Also, PCa patients with high vs. low C1GALT1 expression also had increased mortality, HR=2.28 (FIG. 7D) (the low C1GALT1 expression means an average of C1GALT1 mRNA expression level in the in the tumor not significantly higher than the paired adjacent normal tissue of the same PCa patient). In an examination of the association between galectin-4 and C1GALT1 in PCa patients, results showed that patients with tumors concurrently overexpressing galectin-4 and C1GALT1 had the highest HR of 15.8 in PCa patients and the worst overall survival (FIG. 7D-F). Moreover, the expression level of galectin-4 was also significantly correlated with C1GALT1 expression (FIG. 7G). Together, these data suggest that galectin-4 and C1GALT1 coexpression is elevated in the majority of mCRPC cases and strongly predicts poor survival in PCa patients.

3. Discussion

Elevation of O-glycosylation has been implicated in a wide range of cancers. Typical features of glycosylation occurring in cancer cells include incomplete or short O-glycans, such as T and sialyl-T antigens, unlike normal cells which express core 3 or core 4-derived long-chain O-glycans (30, 31). The biosynthesis of abnormal glycans is an intricate process requiring the coordinated action of multiple glycosyltransferases as well as the availability of substrates for the transferases. In hormone-refractory PCa cells and advanced stages of primary prostate tumors, mislocalization of GCNT1 to the endoplasmic reticulum due to dysfunction of Golgi matrix protein giantin led to reduced expression of core 2-associated polylactosamine, while T antigen was enhanced, which allowed cells to evade galectin-1-induced apoptosis (32). Differential expression of glycosyltransferases can also affect the glycophenotype; for example, terminal modification by ST3GAL1 competes for core 1 substrate with GCNT1 to prevent core 2 structure and promote sialyl-T antigen development (33). On the other hand, the mRNA level of the UDP-Gal transporter is increased in colon cancer tissue, and transfection with UDP-Gal transporter cDNA led to the expression of T antigen (34). Convergence of clinical analysis and our data indicated that elevated galectin-4 in PCa was associated with the development of short chain core 1 O-glycans by increasing C1GALT1 and ST3GAL1 and lowering GCNT1, resulting in a change of surface O-glycosylation for more galectin-4 binding. Herein, MYC serves as a regulator of a hierarchical control system through direct DNA-binding coordinating the gene expression of O-glycosylation enzymes to produce essential O-glycan substrates; galectin-4 expression further enhances the MYC-mediated transcription of O-glycosylation enzymes and alters surface O-glycosylation for more galectin-4 binding. In agreement, previous study indicated that ST3GAL1 are highly expressed in colon cancer cells and transcriptionally up-regulated by MYC (35). The MYC proto-oncogene is frequently activated in human cancers, including PCa. Accordingly, investigations of clinical PCa tissues have revealed that expression of MYC is closely correlated with CRPC (36). Amplification of the MYC gene is detected in up to 72% of hormone-refractory PCa tissues as determined by fluorescence in situ hybridization analysis; MYC gene amplification was detected in 33% clinical PCa before ADT and was significantly increased to 57% after ADT (37, 38). Our data indicated that MYC activation upregulates C1GALT1-mediated O-glycosylation in PCa cells; moreover, galectin-4 expression synergizes with MYC function to promote PCa progression.

Upregulated C1GALT1 is more associated with mCRPC than localized tumors, suggesting that core 1 O-glycosylation may mediate the dissemination and adaptation of cancer cells to distant tissues. In line with this supposition, genetic deletion of C1galt1 in the mammary epithelium hampered the carcinogenesis in the MMTV-PyMT mouse mammary tumor model (39). In colorectal tumors, increased C1GALT1 expression is associated with poor survival, while C1GALT1 overexpression modifies O-glycans on FGFR2 and enhances its phosphorylation which promotes invasive behavior and stem-like properties in colon cancer cells (40). Also, high ST3GAL1 expression in glioblastoma is associated with poor survival, and ST3GAL1 knockdown suppresses the CSC property and prolongs survival in a mouse model (41). Benzyl-α-GalNAc treatment in PCa cells significantly impaired the biosynthesis of α2,3-sialyl-T antigen and suppressed galectin-4 activity, suggesting a selective binding of galectin-4 to α2,3-sialyl-T antigen over T antigen. It also suggested that cellular metabolism of benzyl-α-GalNAc to Galβ1-3GalNAc-α-O-benzyl may act as a potent inhibitor for the α2,3-sialyltransferase activity thus depleted the sialyation and changed the glycan phenotype of cell surface proteins (42). In this study, we demonstrated that α2,3-sialylated core 1 O-glycosylation mediates the development of CRPC and metastasis through galectin-4 interaction with α2,3-sialylated core 1-derived O-glycans and the resulting RTK activation. Using the LNCaP orthotopic tumor model for castration-resistant prostate progression, we demonstrated that the galectin-4-glycan interaction not only promotes PCa metastasis but also drives CRPC development. HER2/3 activation is upregulated in PCa patients receiving ADT, and this finding led to the use of a combination strategy of ADT and HER2/3 inhibitors, such as abiraterone plus lapatinib, in a preclinical study (5). However, the galectin-4 involvement may simultaneously activate multiple RTKs, accounting for progression and resistance to ADT and HER2/3 targeted therapy.

Our in silico analysis of published clinical datasets and the results of our experiments suggest that development of CRPC, at least in a subpopulation of PCa patients, is causatively associated with a repercussive rise of galectin-4 following ADT. In agreement with our data, a recent discovery highlighted that ~30% outliers of CRPC aberrantly express a gastrointestinal (GI)-lineage transcriptome, including LGALS4 (galectin-4), HNF4G, HNF1A, and SPINK1 (43). The galectin-4-induced aggressive behaviors were further supported by increased SOX9 expression. SOX9 has been identified as a PCa stem cell-associated molecule expressed in ALDH$^{hi}$, CD44±, α2β1$^+$ PCa, while downregulating SOX9 reduces tumorsphere formation and in vivo tumorigenicity (44).

Malignant transformation is connected with changes in the O-glycosylation of surface proteins probably by interacting with lectins, which in turn contribute to the metastatic behavior and castration resistance of cancer cells, and therefore tumor-associated carbohydrate antigens could serve as diagnostic and therapeutic targets. For example, it has been demonstrated that CD176 antiserum inhibits the growth and spread of CD176±leukemic cells in the bone marrow, spleen, liver, and lung, therefore prolonging the survival time of leukemic mice (45). Also, T antigen has been found to be conjugated to CSC markers, e.g., CD44 for colon cancer, MUC1 for breast cancer, or CD34 for leukemia, suggesting that T antigen per se may also be a marker of CSC (46). In this study, our data demonstrated that galectin-4 engages with C1GALT1-dependent glycan modifications of RTKs resulting in their activation, enhancing the activity of the AR pathway and also driving castration resistance and metastasis. Therefore, blockade of the galectin-glycan interaction may suppress metastatic CRPC progression.

REFERENCES

1. Buttigliero, C., Tucci, M., Bertaglia, V., Vignani, F., Bironzo, P., Di Maio, M., and Scagliotti, G. V. (2015) Understanding and overcoming the mechanisms of primary and acquired resistance to abiraterone and enzalutamide in castration resistant prostate cancer. *Cancer Treat Rev* 41, 884-892
2. Mellinghoff, I. K., Vivanco, I., Kwon, A., Tran, C., Wongvipat, J., and Sawyers, C. L. (2004) HER2/neu kinase-dependent modulation of androgen receptor function through effects on DNA binding and stability. *Cancer Cell* 6, 517-527
3. Signoretti, S., Montironi, R., Manola, J., Altimari, A., Tam, C., Bubley, G., Balk, S., Thomas, G., Kaplan, I., Hlatky, L., Hahnfeldt, P., Kantoff, P., and Loda, M. (2000) Her-2-neu expression and progression toward androgen independence in human prostate cancer. *J Natl Cancer Inst* 92, 1918-1925
4. Craft, N., Shostak, Y., Carey, M., and Sawyers, C. L. (1999) A mechanism for hormone-independent prostate cancer through modulation of androgen receptor signaling by the HER-2/neu tyrosine kinase. *Nat Med* 5, 280-285
5. Gao, S., Ye, H., Gerrin, S., Wang, H., Sharma, A., Chen, S., Patnaik, A., Sowalsky, A. G., Voznesensky, O., Han, W., Yu, Z., Mostaghel, E. A., Nelson, P. S., Taplin, M. E., Balk, S. P., and Cai, C. (2016) ErbB2 Signaling Increases Androgen Receptor Expression in Abiraterone-Resistant Prostate Cancer. *Clin Cancer Res* 22, 3672-3682
6. Whang, Y. E., Armstrong, A. J., Rathmell, W. K., Godley, P. A., Kim, W. Y., Pruthi, R. S., Wallen, E. M., Crane, J. M., Moore, D. T., Grigson, G., Morris, K., Watkins, C. P., and George, D. J. (2013) A phase II study of lapatinib, a dual EGFR and HER-2 tyrosine kinase inhibitor, in patients with castration-resistant prostate cancer. *Urol Oncol* 31, 82-86
7. Ziada, A., Barqawi, A., Glode, L. M., Varella-Garcia, M., Crighton, F., Majeski, S., Rosenblum, M., Kane, M., Chen, L., and Crawford, E. D. (2004) The use of trastuzumab in the treatment of hormone refractory prostate cancer; phase II trial. *The Prostate* 60, 332-337
8. de Bono, J. S., Bellmunt, J., Attard, G., Droz, J. P., Miller, K., Flechon, A., Sternberg, C., Parker, C., Zugmaier, G., Hersberger-Gimenez, V., Cockey, L., Mason, M., and Graham, J. (2007) Open-label phase II study evaluating the efficacy and safety of two doses of pertuzumab in castrate chemotherapy-naive patients with hormone-refractory prostate cancer. *J Clin Oncol* 25, 257-262
9. Fuster, M. M., and Esko, J. D. (2005) The sweet and sour of cancer: glycans as novel therapeutic targets. *Nat Rev Cancer* 5, 526-542
10. Barrow, H., Guo, X., Wandall, H. H., Pedersen, J. W., Fu, B., Zhao, Q., Chen, C., Rhodes, J. M., and Yu, L. G. (2011) Serum galectin-2, -4, and -8 are greatly increased in colon and breast cancer patients and promote cancer cell adhesion to blood vascular endothelium. *Clin Cancer Res* 17, 7035-7046
11. Agrawal, P., Fontanals-Cirera, B., Sokolova, E., Jacob, S., Vaiana, C. A., Argibay, D., Davalos, V., McDermott, M., Nayak, S., Darvishian, F., Castillo, M., Ueberheide, B., Osman, I., Fenyo, D., Mahal, L. K., and Hernando, E. (2017) A Systems Biology Approach Identifies FUT8 as a Driver of Melanoma Metastasis. *Cancer Cell* 31, 804-819 e807
12. Very, N., Lefebvre, T., and El Yazidi-Belkoura, I. (2018) Drug resistance related to aberrant glycosylation in colorectal cancer. *Oncotarget* 9, 1380-1402

13. Kinney, A. Y., Sahin, A., Vernon, S. W., Frankowski, R. F., Annegers, J. F., Hortobagyi, G. N., Buzdar, A. U., Frye, D. K., and Dhingra, K. (1997) The prognostic significance of sialyl-Tn antigen in women treated with breast carcinoma treated with adjuvant chemotherapy. *Cancer* 80, 2240-2249

14. Zhang, S., Zhang, H. S., Cordon-Cardo, C., Reuter, V. E., Singhal, A. K., Lloyd, K. O., and Livingston, P. O. (1997) Selection of tumor antigens as targets for immune attack using immunohistochemistry: II. Blood group-related antigens. *Int J Cancer* 73, 50-56

15. Reticker-Flynn, N. E., and Bhatia, S. N. (2015) Aberrant glycosylation promotes lung cancer metastasis through adhesion to galectins in the metastatic niche. *Cancer Discov* 5, 168-181

16. Lin, W. M., Karsten, U., Goletz, S., Cheng, R. C., and Cao, Y. (2011) Expression of CD176 (Thomsen-Friedenreich antigen) on lung, breast and liver cancer-initiating cells. *Int J Exp Pathol* 92, 97-105

17. Broos, S., Soete, A., Hooghe, B., Moran, R., van Roy, F., and De Bleser, P. (2013) PhysBinder: Improving the prediction of transcription factor binding sites by flexible inclusion of biophysical properties. *Nucleic Acids Res* 41, W531-534

18. Chen, E. Y., Tan, C. M., Kou, Y., Duan, Q., Wang, Z., Meirelles, G. V., Clark, N. R., and Ma'ayan, A. (2013) Enrichr: interactive and collaborative HTML5 gene list enrichment analysis tool. *BMC Bioinformatics* 14, 128

19. Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005) Gene set enrichment analysis: a knowledge-based approach for interpreting genome-wide expression profiles. *Proc Natl Acad Sci USA* 102, 15545-15550

20. Anderson, P. D., McKissic, S. A., Logan, M., Roh, M., Franco, O. E., Wang, J., Doubinskaia, I., van der Meer, R., Hayward, S. W., Eischen, C. M., Eltoum, I. E., and Abdulkadir, S. A. (2012) Nkx3.1 and Myc crossregulate shared target genes in mouse and human prostate tumorigenesis. *J Clin Invest* 122, 1907-1919

21. Cai, C., Wang, H., He, H. H., Chen, S., He, L., Ma, F., Mucci, L., Wang, Q., Fiore, C., Sowalsky, A. G., Loda, M., Liu, X. S., Brown, M., Balk, S. P., and Yuan, X. (2013) ERG induces androgen receptor-mediated regulation of SOX9 in prostate cancer. *J Clin Invest* 123, 1109-1122

22. Taylor, B. S., Schultz, N., Hieronymus, H., Gopalan, A., Xiao, Y., Carver, B. S., Arora, V. K., Kaushik, P., Cerami, E., Reva, B., Antipin, Y., Mitsiades, N., Landers, T., Dolgalev, I., Major, J. E., Wilson, M., Socci, N. D., Lash, A. E., Heguy, A., Eastham, J. A., Scher, H. I., Reuter, V. E., Scardino, P. T., Sander, C., Sawyers, C. L., and Gerald, W. L. (2010) Integrative genomic profiling of human prostate cancer. *Cancer Cell* 18, 11-22

23. Grasso, C. S., Wu, Y. M., Robinson, D. R., Cao, X., Dhanasekaran, S. M., Khan, A. P., Quist, M. J., Jing, X., Lonigro, R. J., Brenner, J. C., Asangani, I. A., Ateeq, B., Chun, S. Y., Siddiqui, J., Sam, L., Anstett, M., Mehra, R., Prensner, J. R., Palanisamy, N., Ryslik, G. A., Vandin, F., Raphael, B. J., Kunju, L. P., Rhodes, D. R., Pienta, K. J., Chinnaiyan, A. M., and Tomlins, S. A. (2012) The mutational landscape of lethal castration-resistant prostate cancer. *Nature* 487, 239-243

24. Glinsky, V. V., Glinsky, G. V., Glinskii, O. V., Huxley, V. H., Turk, J. R., Mossine, V. V., Deutscher, S. L., Pienta, K. J., and Quinn, T. P. (2003) Intravascular metastatic cancer cell homotypic aggregation at the sites of primary attachment to the endothelium. *Cancer Res* 63, 3805-3811

25. Yazawa, E. M., Geddes-Sweeney, J. E., Cedeno-Laurent, F., Walley, K. C., Barthel, S. R., Opperman, M. J., Liang, J., Lin, J. Y., Schatton, T., Laga, A. C., Mihm, M. C., Qureshi, A. A., Widlund, H. R., Murphy, G. F., and Dimitroff, C. J. (2015) Melanoma Cell Galectin-1 Ligands Functionally Correlate with Malignant Potential. *J Invest Dermatol* 135, 1849-1862

26. Tsai, C. H., Tzeng, S. F., Chao, T. K., Tsai, C. Y., Yang, Y. C., Lee, M. T., Hwang, J. J., Chou, Y. C., Tsai, M. H., Cha, T. L., and Hsiao, P. W. (2016) Metastatic Progression of Prostate Cancer Is Mediated by Autonomous Binding of Galectin-4-O-Glycan to Cancer Cells. *Cancer Res* 76, 5756-5767

27. Vidal, S. J., Rodriguez-Bravo, V., Quinn, S. A., Rodriguez-Barrueco, R., Lujambio, A., Williams, E., Sun, X., de la Iglesia-Vicente, J., Lee, A., Readhead, B., Chen, X., Galsky, M., Esteve, B., Petrylak, D. P., Dudley, J. T., Rabadan, R., Silva, J. M., Hoshida, Y., Lowe, S. W., Cordon-Cardo, C., and Domingo-Domenech, J. (2015) A targetable GATA2-IGF2 axis confers aggressiveness in lethal prostate cancer. *Cancer Cell* 27, 223-239

28. Larsimont, J. C., Youssef, K. K., Sanchez-Danes, A., Sukumaran, V., Defrance, M., Delatte, B., Liagre, M., Baatsen, P., Marine, J. C., Lippens, S., Guerin, C., Del Marmol, V., Vanderwinden, J. M., Fuks, F., and Blanpain, C. (2015) Sox9 Controls Self-Renewal of Oncogene Targeted Cells and Links Tumor Initiation and Invasion. *Cell Stem Cell* 17, 60-73

29. Sears, R., Nuckolls, F., Haura, E., Taya, Y., Tamai, K., and Nevins, J. R. (2000) Multiple Ras-dependent phosphorylation pathways regulate Myc protein stability. *Genes Dev* 14, 2501-2514

30. Glinsky, V. V., Glinsky, G. V., Rittenhouse-Olson, K., Huflejt, M. E., Glinskii, O. V., Deutscher, S. L., and Quinn, T. P. (2001) The role of Thomsen-Friedenreich antigen in adhesion of human breast and prostate cancer cells to the endothelium. *Cancer Res* 61, 4851-4857

31. Storr, S. J., Royle, L., Chapman, C. J., Hamid, U. M., Robertson, J. F., Murray, A., Dwek, R. A., and Rudd, P. M. (2008) The O-linked glycosylation of secretory/shed MUC1 from an advanced breast cancer patient's serum. *Glycobiology* 18, 456-462

32. Petrosyan, A., Holzapfel, M. S., Muirhead, D. E., and Cheng, P. W. (2014) Restoration of compact Golgi morphology in advanced prostate cancer enhances susceptibility to galectin-1-induced apoptosis by modifying mucin O-glycan synthesis. *Mol Cancer Res* 12, 1704-1716

33. Dalziel, M., Whitehouse, C., McFarlane, I., Brockhausen, I., Gschmeissner, S., Schwientek, T., Clausen, H., Burchell, J. M., and Taylor-Papadimitriou, J. (2001) The relative activities of the C2GnT1 and ST3Gal-I glycosyltransferases determine O-glycan structure and expression of a tumor-associated epitope on MUC1. *J Biol Chem* 276, 11007-11015

34. Kumamoto, K., Goto, Y., Sekikawa, K., Takenoshita, S., Ishida, N., Kawakita, M., and Kannagi, R. (2001) Increased expression of UDP-galactose transporter messenger RNA in human colon cancer tissues and its implication in synthesis of Thomsen-Friedenreich antigen and sialyl Lewis A/X determinants. *Cancer Res* 61, 4620-4627

35. Sakuma, K., Aoki, M., and Kannagi, R. (2012) Transcription factors c-Myc and CDX2 mediate E-selectin ligand expression in colon cancer cells undergoing EGF/ bFGF-induced epithelial-mesenchymal transition. *Proc Natl Acad Sci USA* 109, 7776-7781
36. Hawksworth, D., Ravindranath, L., Chen, Y., Furusato, B., Sesterhenn, I. A., McLeod, D. G., Srivastava, S., and Petrovics, G. (2010) Overexpression of C-MYC oncogene in prostate cancer predicts biochemical recurrence. *Prostate Cancer Prostatic Dis* 13, 311-315
37. Nupponen, N. N., Kakkola, L., Koivisto, P., and Visakorpi, T. (1998) Genetic alterations in hormone-refractory recurrent prostate carcinomas. *Am J Pathol* 153, 141-148
38. Kaltz-Wittmer, C., Klenk, U., Glaessgen, A., Aust, D. E., Diebold, J., Lohrs, U., and Baretton, G. B. (2000) FISH analysis of gene aberrations (MYC, CCND1, ERBB2, RB, and AR) in advanced prostatic carcinomas before and after androgen deprivation therapy. *Lab Invest* 80, 1455-1464
39. Song, K., Herzog, B. H., Fu, J., Sheng, M., Bergstrom, K., McDaniel, J. M., Kondo, Y., McGee, S., Cai, X., Li, P., Chen, H., and Xia, L. (2015) Loss of Core 1-derived O-Glycans Decreases Breast Cancer Development in Mice. *J Biol Chem* 290, 20159-20166
40. Hung, J. S., Huang, J., Lin, Y. C., Huang, M. J., Lee, P. H., Lai, H. S., Liang, J. T., and Huang, M. C. (2014) C1GALT1 overexpression promotes the invasive behavior of colon cancer cells through modifying O-glycosylation of FGFR2. *Oncotarget* 5, 2096-2106
41. Chong, Y. K., Sandanaraj, E., Koh, L. W., Thangaveloo, M., Tan, M. S., Koh, G. R., Toh, T. B., Lim, G. G., Holbrook, J. D., Kon, O. L., Nadarajah, M., Ng, I., Ng, W. H., Tan, N. S., Lim, K. L., Tang, C., and Ang, B. T. (2016) ST3GAL1-Associated Transcriptomic Program in Glioblastoma Tumor Growth, Invasion, and Prognosis. *J Natl Cancer Inst* 108
42. Ulloa, F., Franci, C., and Real, F. X. (2000) GalNAc-alpha-O-benzyl inhibits sialylation of de Novo synthesized apical but not basolateral sialoglycoproteins and blocks lysosomal enzyme processing in a post-trans-Golgi network compartment. *J Biol Chem* 275, 18785-18793
43. Shukla, S., Cyrta, J., Murphy, D. A., Walczak, E. G., Ran, L., Agrawal, P., Xie, Y., Chen, Y., Wang, S., Zhan, Y., Li, D., Wong, E. W. P., Sboner, A., Beltran, H., Mosquera, J. M., Sher, J., Cao, Z., Wongvipat, J., Koche, R. P., Gopalan, A., Zheng, D., Rubin, M. A., Scher, H. I., Chi, P., and Chen, Y. (2017) Aberrant Activation of a Gastrointestinal Transcriptional Circuit in Prostate Cancer Mediates Castration Resistance. *Cancer Cell* 32, 792-806 e797
44. Chen, X., Li, Q., Liu, X., Liu, C., Liu, R., Rycaj, K., Zhang, D., Liu, B., Jeter, C., Calhoun-Davis, T., Lin, K., Lu, Y., Chao, H. P., Shen, J., and Tang, D. G. (2016) Defining a Population of Stem-like Human Prostate Cancer Cells That Can Generate and Propagate Castration-Resistant Prostate Cancer. *Clin Cancer Res* 22, 4505-4516
45. Yi, B., Zhang, Z., Zhang, M., Schwartz-Albiez, R., and Cao, Y. (2013) CD176 antiserum treatment leads to a therapeutic response in a murine model of leukemia. *Oncol Rep* 30, 1841-1847
46. Karsten, U., and Goletz, S. (2013) What makes cancer stem cell markers different? *Springerplus* 2, 301

What is claimed is:

1. A method for predicting prognosis of prostate cancer, comprising
   (i) providing a prostate tumor sample from a subject afflicted with prostate cancer; and
   (ii) detecting a core 1 beta-3-galactosyltransferase (C1GALT1) gene product and a galectin-4 gene product in the prostate tumor sample; and
   (iii) comparing the results of the detection with a reference level and predicting prognosis for the subject based on the results of the comparison, wherein an elevated level of both the C1GALT1 gene product and the galectin-4 gene product is indicative of a more negative prognosis when compared to an elevated level of the C1GALT1 gene product alone or an elevated level of the galectin-4 gene product alone.

2. The method of claim 1, wherein the gene product includes a protein or a RNA transcript.

3. The method of claim 1, wherein the C1GALT1 gene product is detected with a first agent that specifically binds to the C1GALT1 gene product, and the galectin-4 gene product is detected with a second agent that specifically binds to the galectin-4 gene product.

4. The method of claim 3, wherein the first agent is an antibody and/or the second agent is an antibody.

5. The method of claim 1, wherein the detection is performed by a mass spectrometric assay or an immunoassay.

6. The method of claim 1, wherein the negative prognosis is selected from the group consisting of a reduced survival rate, an increased tumor size or number, an increased risk of metastasis, an increased risk of resistance to androgen deprivation therapy (ADT), an increased risk of relapse, and any combination thereof.

7. A method for monitoring progression of prostate cancer in a patient afflicted with prostate cancer, comprising
   (a) providing a first prostate tumor sample from the patient at a first time point;
   (b) providing a second prostate tumor sample from the patient at a second time point, which is later than the first time point;
   (c) detecting the levels of a C1GALT1 gene product and a galectin-4 gene product in the first and second samples; and
   (d) determining prostate cancer progression in the patient based on the levels of the C1GALT1 gene product and the galectin-4 gene product in the first and second samples, wherein an elevated level of both the C1GALT1 gene product and the galectin-4 gene product in the second sample as compared to that in the first sample is indicative of a higher risk for prostate cancer progression when compared to an elevated level of the C1GALT1 gene product alone or an elevated level of the galectin-4 gene product alone in the second sample as compared to that in the first sample.

8. The method of claim 7, wherein the gene product includes a protein or a RNA transcript.

9. The method of claim 7, wherein the C1GALT1 gene product is detected with a first agent that specifically binds to the C1GALT1 gene product, and the galectin-4 gene product is detected with a second agent that specifically binds to the galectin-4 gene product.

10. The method of claim 9, wherein the first agent is an antibody and/or the second agent is an antibody.

11. The method of claim 7, wherein the detection is performed by a mass spectrometric assay or an immunoassay.

12. A method for predicting survival of prostate cancer, comprising
   (i) providing a prostate tumor sample from a patient afflicted with prostate cancer;
   (ii) detecting a level of a core 1 beta-3-galactosyltransferase (C1GALT1) mRNA and a level of a galectin-4 mRNA in the prostate tumor sample using quantitative RT-PCR;
   (iii) comparing the detected level of the C1GALT1 mRNA with a reference level of C1GALT1 mRNA from a healthy prostate sample, and comparing the detected level of the galectin-4 mRNA with a reference level of galectin-4 mRNA from a healthy prostate sample;
   (iv) predicting survival of the patient based on the comparison, including predicting a relatively higher risk for poor survival of the patient if the detected level of C1GALT1 mRNA in the prostate tumor sample exceeds the reference level of C1GALT1 mRNA and the detected level of galectin-4 mRNA in the prostate tumor sample exceeds the reference level of galectin-4, and otherwise predicting a relatively lower risk for poor survival of the patient if the detected level of C1GALT1 mRNA in the prostate tumor sample exceeds the reference level of C1GALT1 mRNA but the detected level of galectin-4 mRNA in the prostate tumor sample does not exceed the reference level of galectin-4, the detected level of galectin-4 mRNA in the prostate tumor sample exceeds the reference level of galectin-4 mRNA but the detected level of C1GALT1 mRNA in the prostate tumor sample does not exceed the reference level of C1GALT1, or the detected level of C1GALT1 mRNA in the prostate tumor sample does not exceed the reference level of C1GALT1 mRNA and the detected level of galectin-4 mRNA in the prostate tumor sample does not exceed the reference level of galectin-4.

13. The method of claim 12, wherein the quantitative RT-PCR is carried out by using C1GALT1 forward primer 5'-TCCCTTTGTGCCAGAACACC (SEQ ID NO: 1) and C1GALT1 reverse primer 5'-AGCAACCAGGACCCTC-TACA (SEQ ID NO: 2), and galectin-4 forward primer 5'-GATGCCACCTTACCCTGGTC (SEQ ID NO: 7) and galectin-4 reverse primer 5'-CCTTGCAGCCTCCCGAAATA (SEQ ID NO: 8).

14. The method of claim 12, wherein
   the patient has a hazard ratio (HR) of 15.8 for poor survival if the detected level of C1GALT1 mRNA in the prostate tumor sample exceeds the reference level of C1GALT1 mRNA and the detected level of galectin-4 mRNA in the prostate tumor sample exceeds the reference level of galectin-4;
   the patient has a HR of 2.28 for poor survival if the detected level of C1GALT1 mRNA in the prostate tumor sample exceeds the reference level of C1GALT1 mRNA but the detected level of galectin-4 mRNA in the prostate tumor sample does not exceed the reference level of galectin-4; or
   the patient of a low risk for poor survival has a HR of 2.975 for poor survival if the detected level of galectin-4 mRNA in the prostate tumor sample exceeds the reference level of galectin-4 mRNA but the detected level of C1GALT1 mRNA in the prostate tumor sample does not exceed the reference level of C1GALT1.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: C1GALT1 forward primer

<400> SEQUENCE: 1
tccctttgtg ccagaacacc                                               20

<210> SEQ ID NO 2
<211> LENGTH: 20
<212> TYPE: DNA
<213> ORGANISM: Artificial Sequence
<220> FEATURE:
<223> OTHER INFORMATION: C1GALT1 reverse primer

<400> SEQUENCE: 2
agcaaccagg accctctaca                                               20

<210> SEQ ID NO 3
<211> LENGTH: 20
<212> TYPE: DNA
<213> ORGANISM: Artificial Sequence
<220> FEATURE:
<223> OTHER INFORMATION: AR forward primer

<400> SEQUENCE: 3
cgttcttcaa gcccaagtgc                                               20

<210> SEQ ID NO 4
<211> LENGTH: 20

```
<212> TYPE: DNA
<213> ORGANISM: Artificial Sequence
<220> FEATURE:
<223> OTHER INFORMATION: AR reverse primer

<400> SEQUENCE: 4
atgggcagct tgatgactgg                                              20

<210> SEQ ID NO 5
<211> LENGTH: 20
<212> TYPE: DNA
<213> ORGANISM: Artificial Sequence
<220> FEATURE:
<223> OTHER INFORMATION: PSA forward primer

<400> SEQUENCE: 5
gtatcacgtc atggggcagt                                              20

<210> SEQ ID NO 6
<211> LENGTH: 20
<212> TYPE: DNA
<213> ORGANISM: Artificial Sequence
<220> FEATURE:
<223> OTHER INFORMATION: PSA reverse primer

<400> SEQUENCE: 6
ggttgatagg ggtgctcagg                                              20

<210> SEQ ID NO 7
<211> LENGTH: 20
<212> TYPE: DNA
<213> ORGANISM: Artificial Sequence
<220> FEATURE:
<223> OTHER INFORMATION: galectin-4 forward primer

<400> SEQUENCE: 7
gatgccacct taccctggtc                                              20

<210> SEQ ID NO 8
<211> LENGTH: 20
<212> TYPE: DNA
<213> ORGANISM: Artificial Sequence
<220> FEATURE:
<223> OTHER INFORMATION: galectin-4 reverse primer

<400> SEQUENCE: 8
ccttgcagcc tcccgaaata                                              20

<210> SEQ ID NO 9
<211> LENGTH: 20
<212> TYPE: DNA
<213> ORGANISM: Artificial Sequence
<220> FEATURE:
<223> OTHER INFORMATION: SOX9 forward primer

<400> SEQUENCE: 9
tctgaacgag agcgagaagc                                              20

<210> SEQ ID NO 10
<211> LENGTH: 20
<212> TYPE: DNA
<213> ORGANISM: Artificial Sequence
<220> FEATURE:
<223> OTHER INFORMATION: SOX reverse primer

<400> SEQUENCE: 10
```

```
ccgttcttca ccgacttcct                                                    20
```

<210> SEQ ID NO 11
<211> LENGTH: 20
<212> TYPE: DNA
<213> ORGANISM: Artificial Sequence
<220> FEATURE:
<223> OTHER INFORMATION: ST3GAL1 forward primer

<400> SEQUENCE: 11

```
ggcaacctga gggagtcttc                                                    20
```

<210> SEQ ID NO 12
<211> LENGTH: 20
<212> TYPE: DNA
<213> ORGANISM: Artificial Sequence
<220> FEATURE:
<223> OTHER INFORMATION: ST3GAL1 reverse primer

<400> SEQUENCE: 12

```
gtacaccaga tggtgggtgg                                                    20
```

<210> SEQ ID NO 13
<211> LENGTH: 20
<212> TYPE: DNA
<213> ORGANISM: Artificial Sequence
<220> FEATURE:
<223> OTHER INFORMATION: MYC binding site forward primer

<400> SEQUENCE: 13

```
agcaggatca gaaatgcgga                                                    20
```

<210> SEQ ID NO 14
<211> LENGTH: 20
<212> TYPE: DNA
<213> ORGANISM: Artificial Sequence
<220> FEATURE:
<223> OTHER INFORMATION: MYC binding site reverse primer

<400> SEQUENCE: 14

```
ccctaatgcg aaggggtctg                                                    20
```

<210> SEQ ID NO 15
<211> LENGTH: 20
<212> TYPE: DNA
<213> ORGANISM: Artificial Sequence
<220> FEATURE:
<223> OTHER INFORMATION: negative control forward primer

<400> SEQUENCE: 15

```
tggccagcca tgacttatga                                                    20
```

<210> SEQ ID NO 16
<211> LENGTH: 21
<212> TYPE: DNA
<213> ORGANISM: Artificial Sequence
<220> FEATURE:
<223> OTHER INFORMATION: negative control reverse primer

<400> SEQUENCE: 16

```
aaactcgttg gagtaggtcg g                                                  21
```